United States Patent [19]

Rzeszotarski et al.

[11] Patent Number: 4,760,069
[45] Date of Patent: Jul. 26, 1988

[54] OXIMES OF OXYMORPHONE, NALTREXONE AND NALOXONE AS POTENT, SELECTIVE OPIOID RECEPTOR AGONISTS AND ANTAGONISTS

[75] Inventors: Waclaw J. Rzeszotarski, Millersville; Babu J. Mavunkel, Baltimore, both of Md.

[73] Assignee: Nova Pharmaceutical Corporation, Baltimore, Md.

[21] Appl. No.: 778,800

[22] Filed: Sep. 23, 1985

[51] Int. Cl.⁴ .................. A61K 31/485; C07D 489/08
[52] U.S. Cl. ........................................ 514/282; 546/45
[58] Field of Search ........................... 546/45; 514/282

[56] References Cited
U.S. PATENT DOCUMENTS 3,135,758  6/1964  Fishman ................................ 546/45
3,153,042  10/1964 Fishman ................................ 546/45
3,320,262  5/1967  Lewenstein et al. ................. 546/45

OTHER PUBLICATIONS

Rapoport, et al., J. Organic Chem., vol. 15, pp. 1103–1106 (1950).
Bentley, "The Chemistry of the Morphine Alkaloids", Oxford (1954) pp. 180, 259.
Sawa, et al., Tetrahedron, vol. 24, pp. 6185–6196 (1968).
Hahn, et al., J. Pharm. & Pharmacology, vol. 35(17), pp. 833–836 (12/83).
Ko, et al., J. Med. Chem., vol. 27(12), pp. 1727–1729 (12/84).
Koolpe, et al., J. Med. Chem., vol. 28(7), pp. 949–957 (7/85).
Mohamed, et al., Chemical Abstracts, vol. 104, 8886t (196).

Primary Examiner—Nicholas S. Rizzo
Assistant Examiner—Diana G. Rivers
Attorney, Agent, or Firm—Breneman & Georges

[57] ABSTRACT

A potent, selective opioid receptor agonist or antagonist exhibiting properties useful for a long-acting analgesic or opiate abuse treatment agent or appetite suppressant having the general formula:

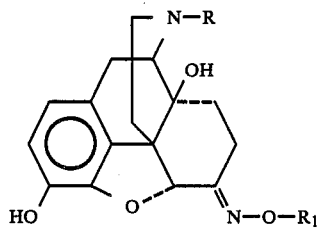

wherein R is methyl, cyclopropylmethyl or allyl, and $R_1$ is an unsubstituted or substituted aryl, aralkyl, heteroaryl, heteroaralkyl or a cycloalkyl group with or without a heteroatom like S,O,N; and the pharmaceutically acceptable salts thereof.

22 Claims, 17 Drawing Sheets

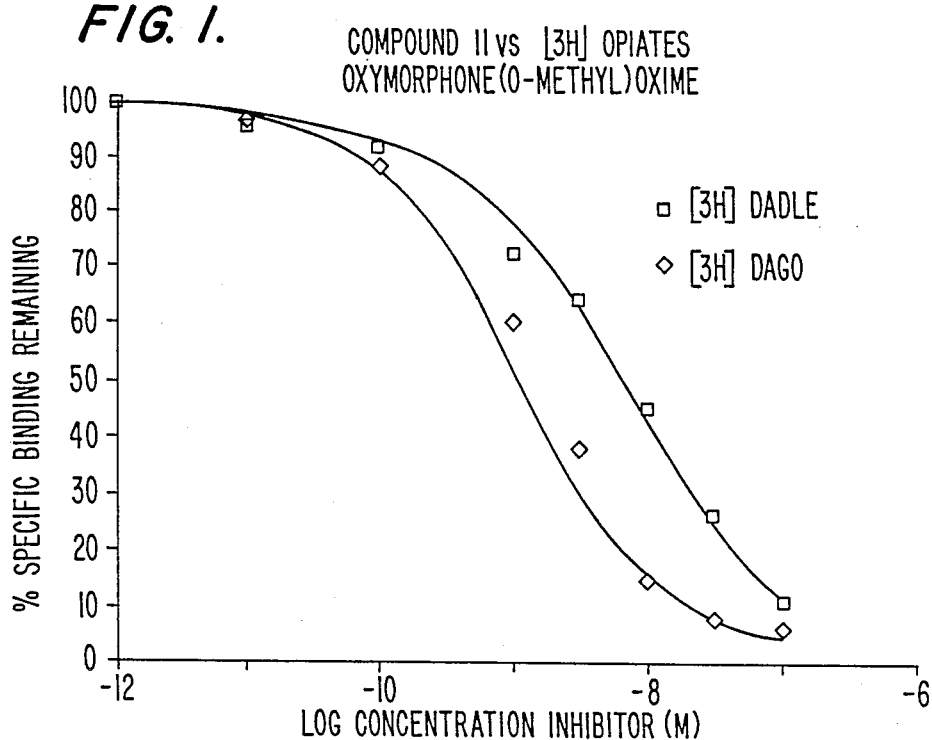
FIG. 1. COMPOUND II vs [3H] OPIATES OXYMORPHONE(O-METHYL)OXIME
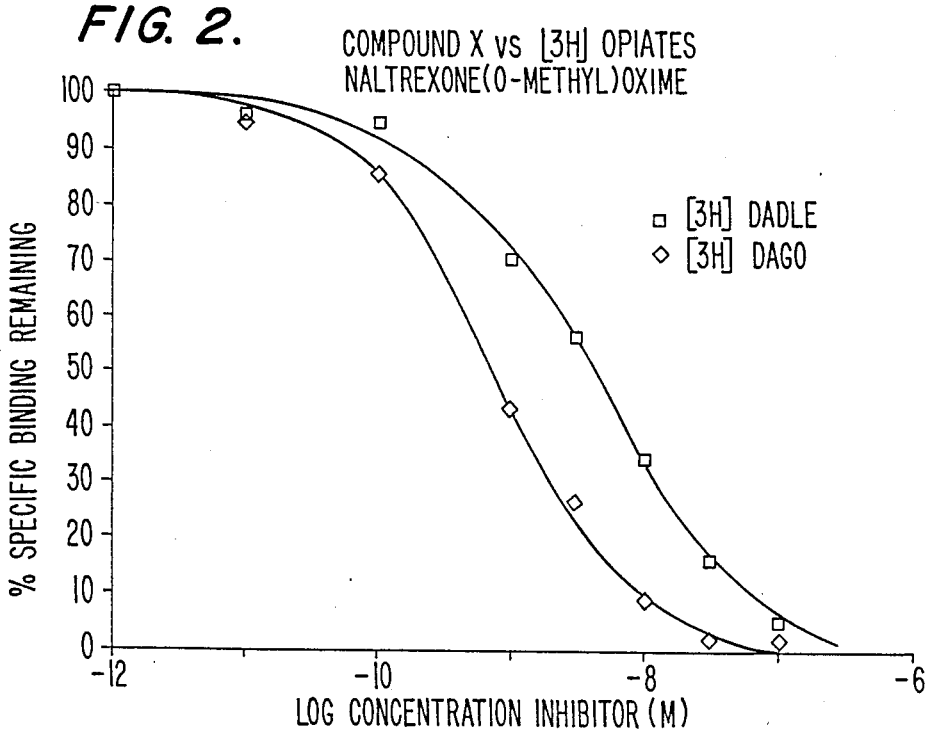
FIG. 2. COMPOUND X vs [3H] OPIATES NALTREXONE(O-METHYL)OXIME

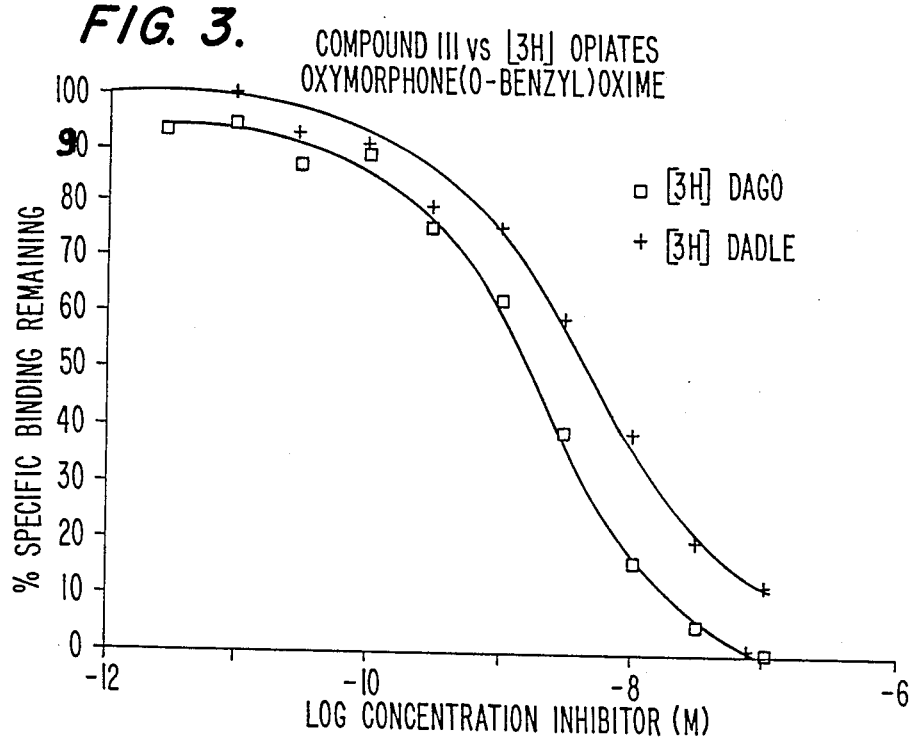
FIG. 3. COMPOUND III vs [3H] OPIATES OXYMORPHONE(O-BENZYL)OXIME
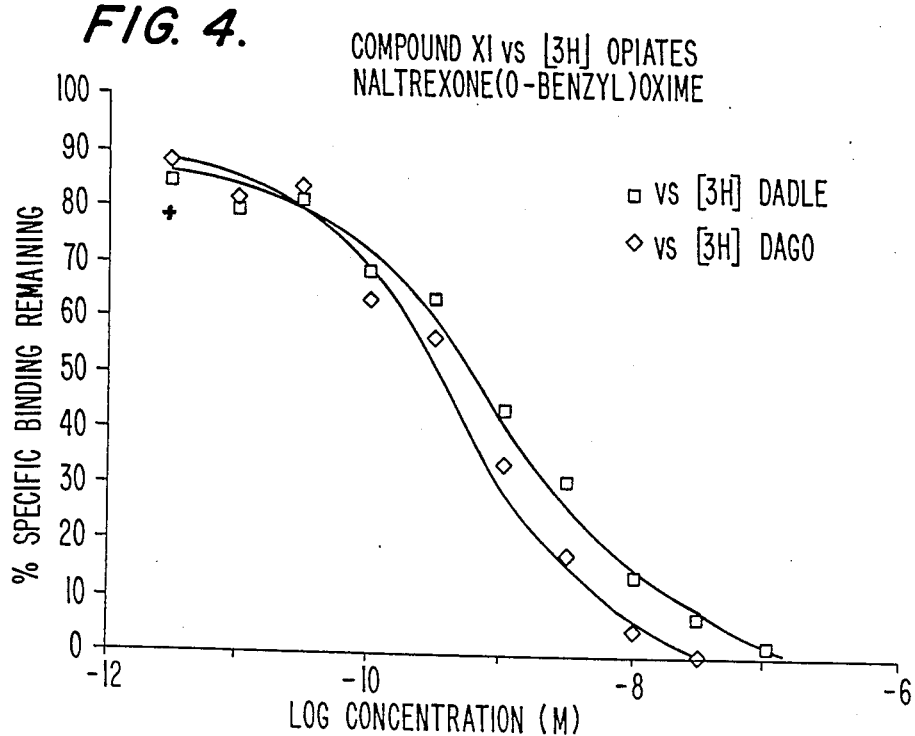
FIG. 4. COMPOUND XI vs [3H] OPIATES NALTREXONE(O-BENZYL)OXIME

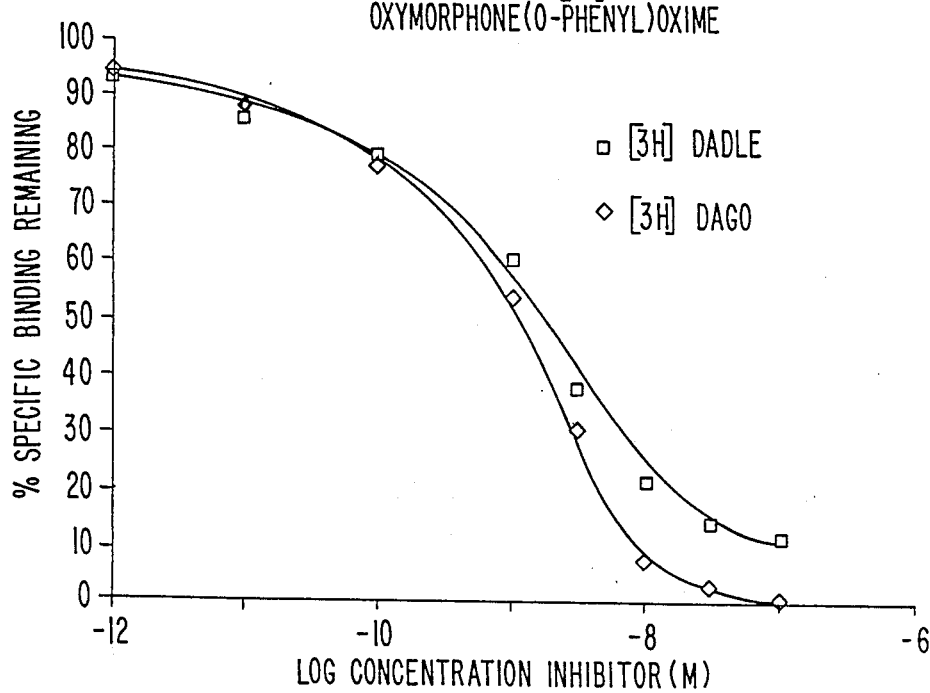
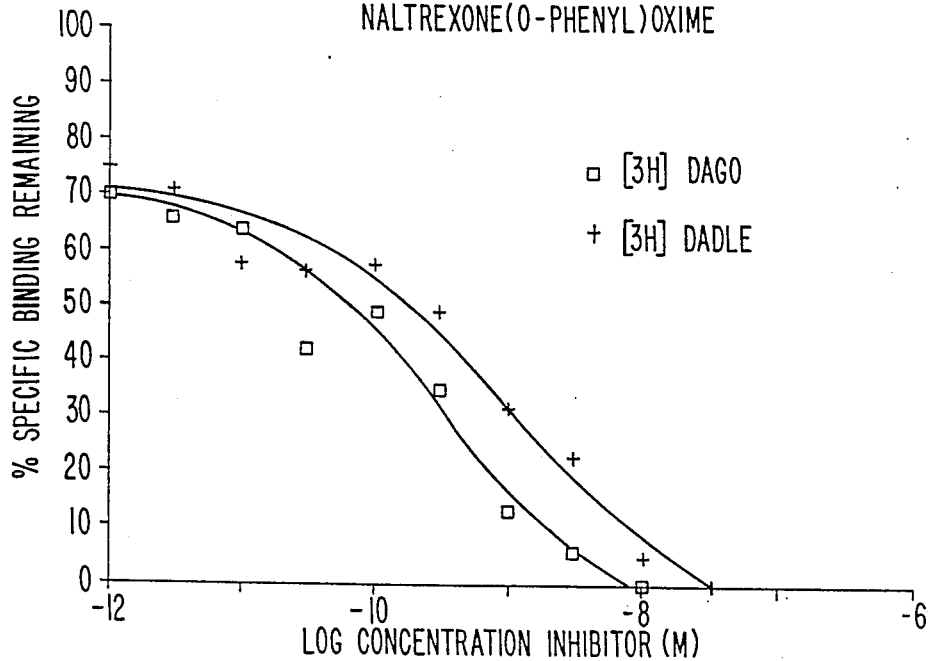

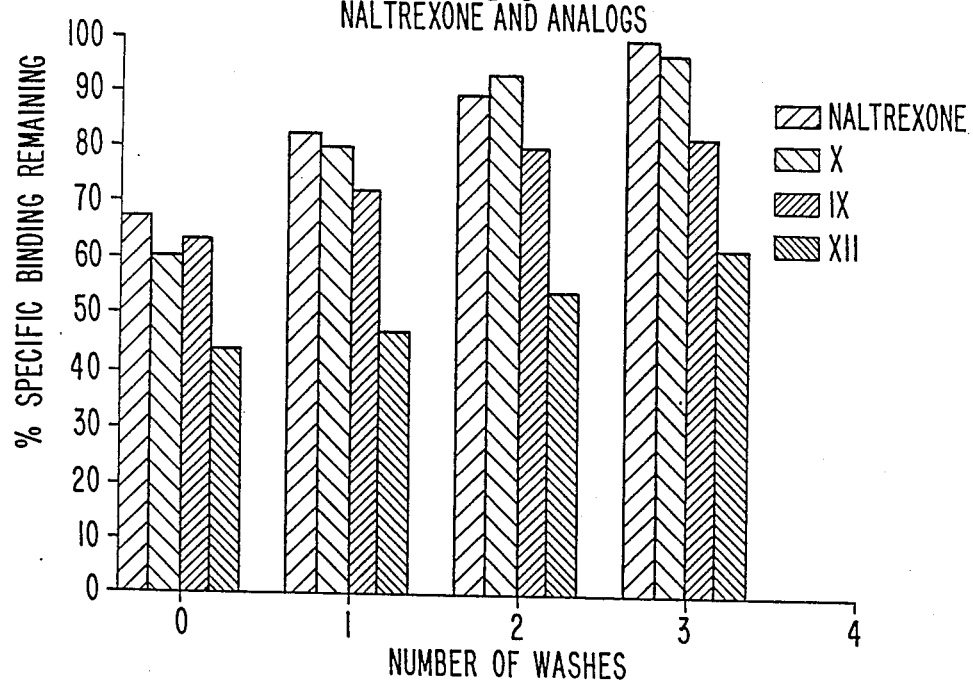
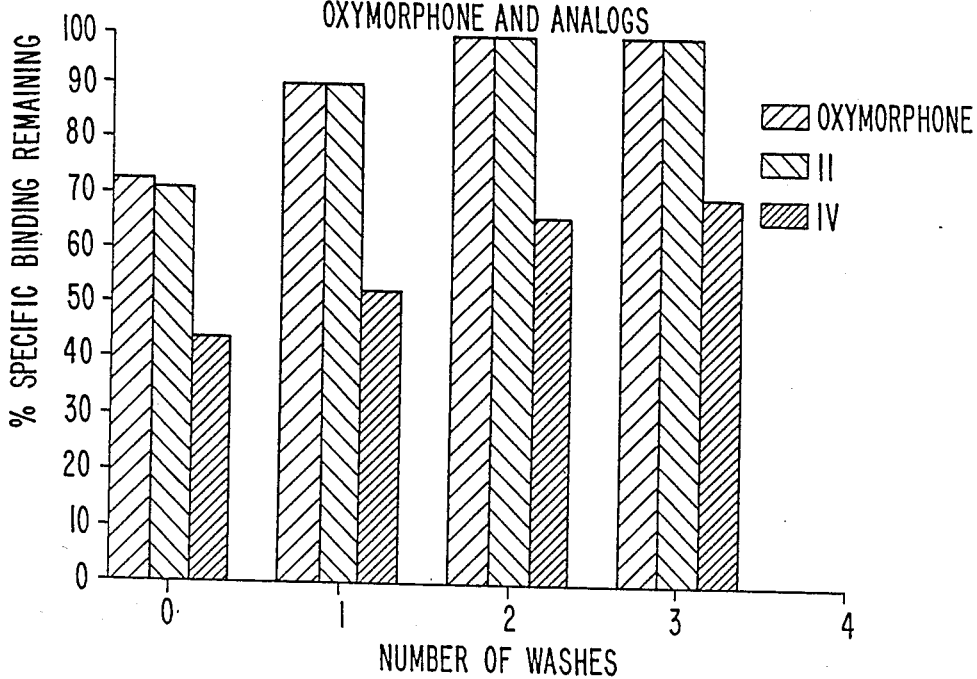

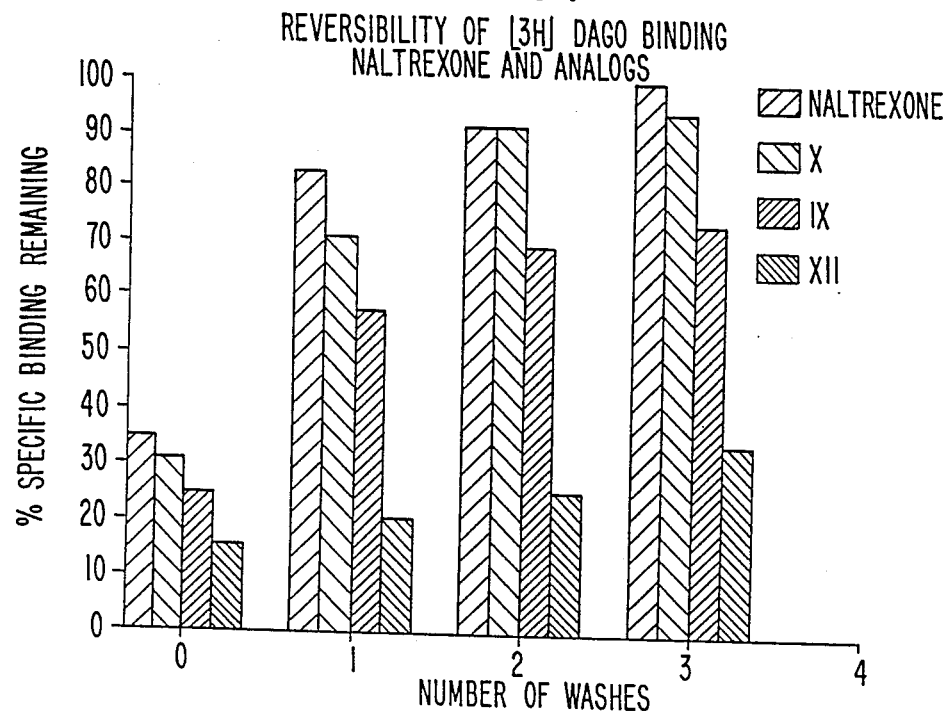
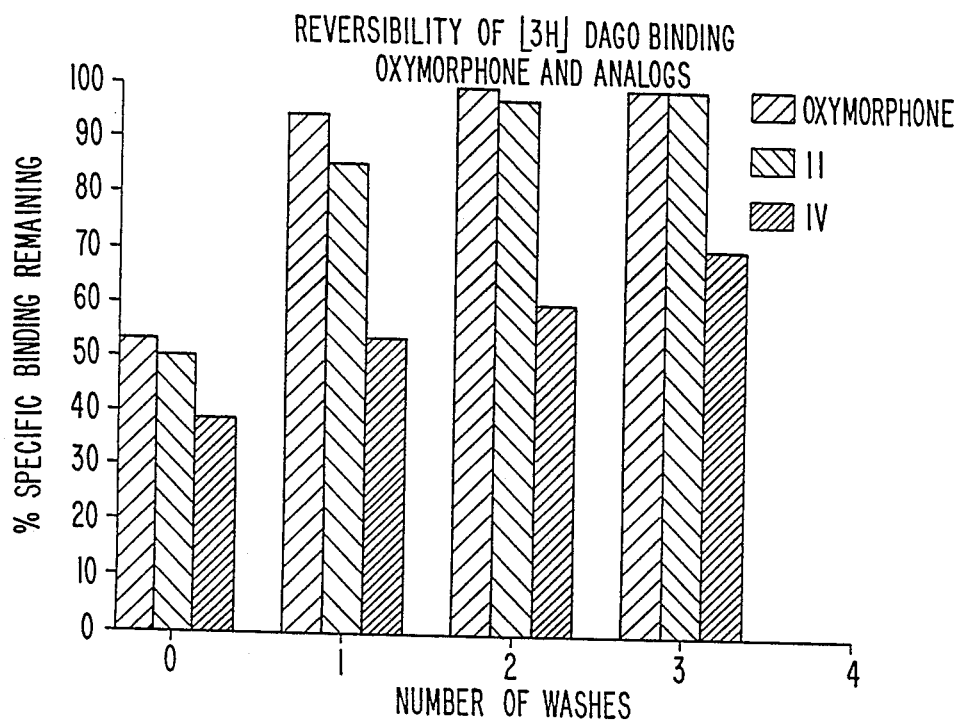

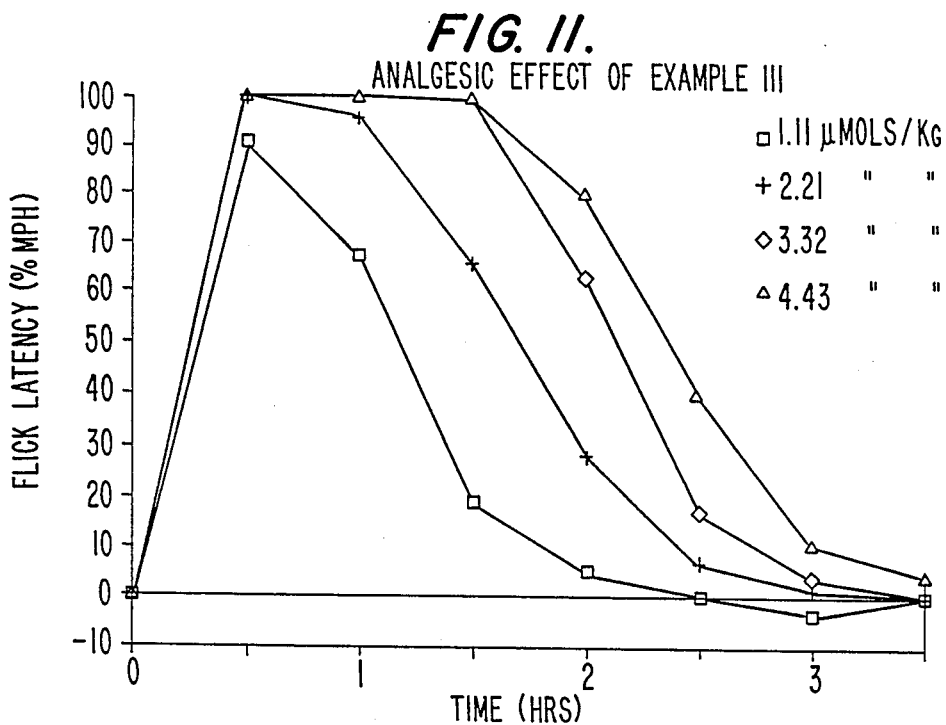
FIG. 11. ANALGESIC EFFECT OF EXAMPLE III
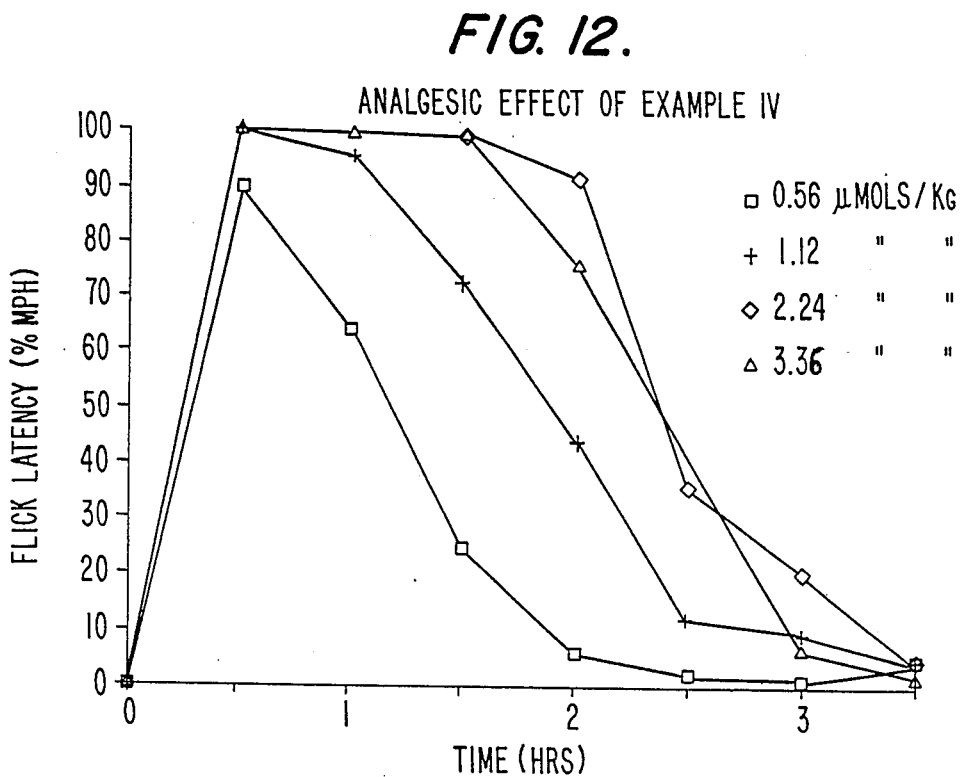
FIG. 12. ANALGESIC EFFECT OF EXAMPLE IV

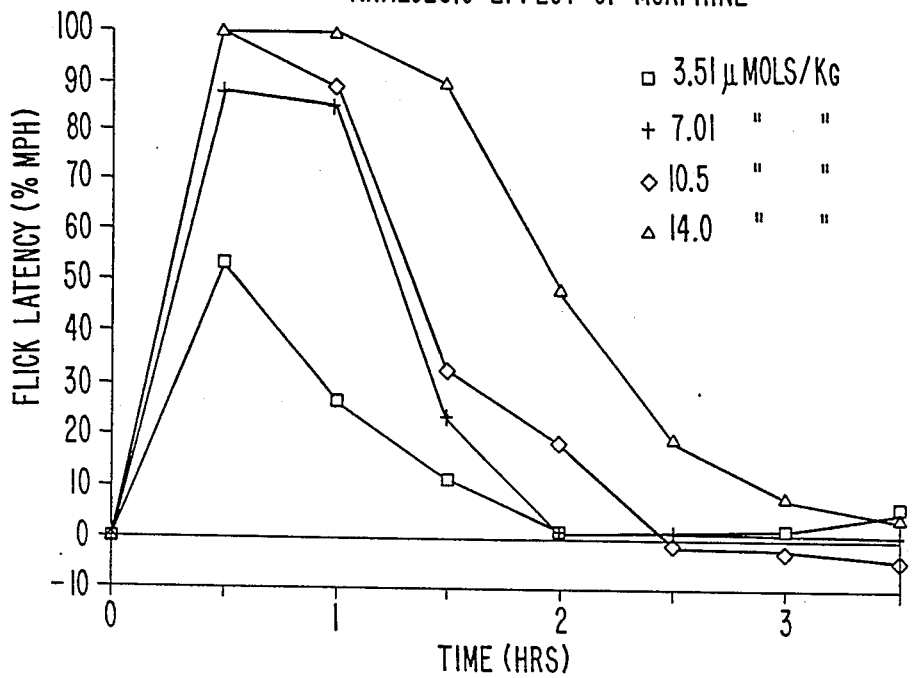
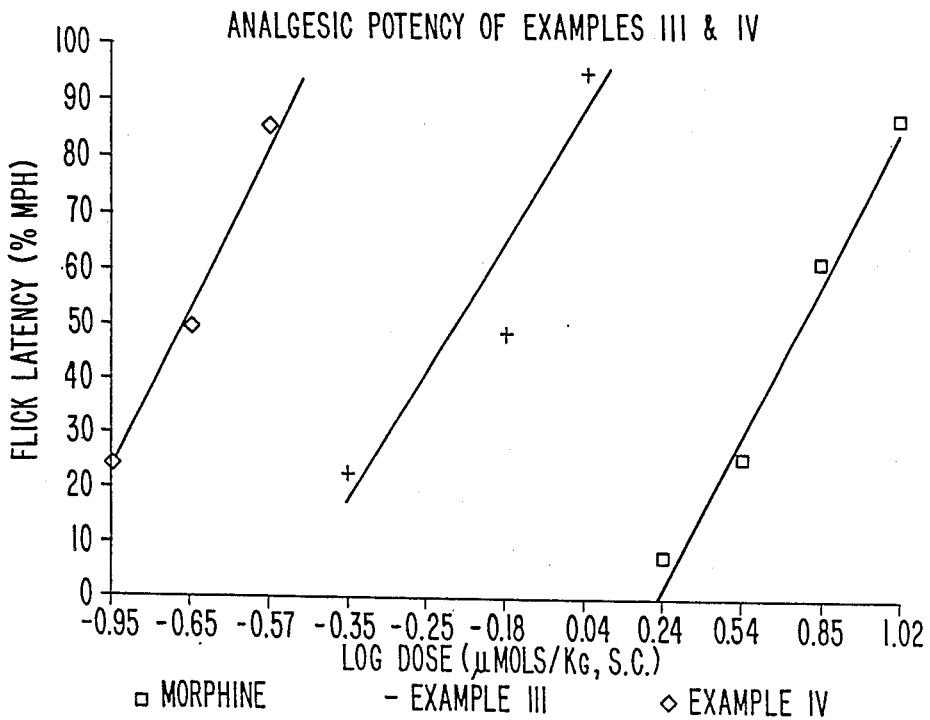

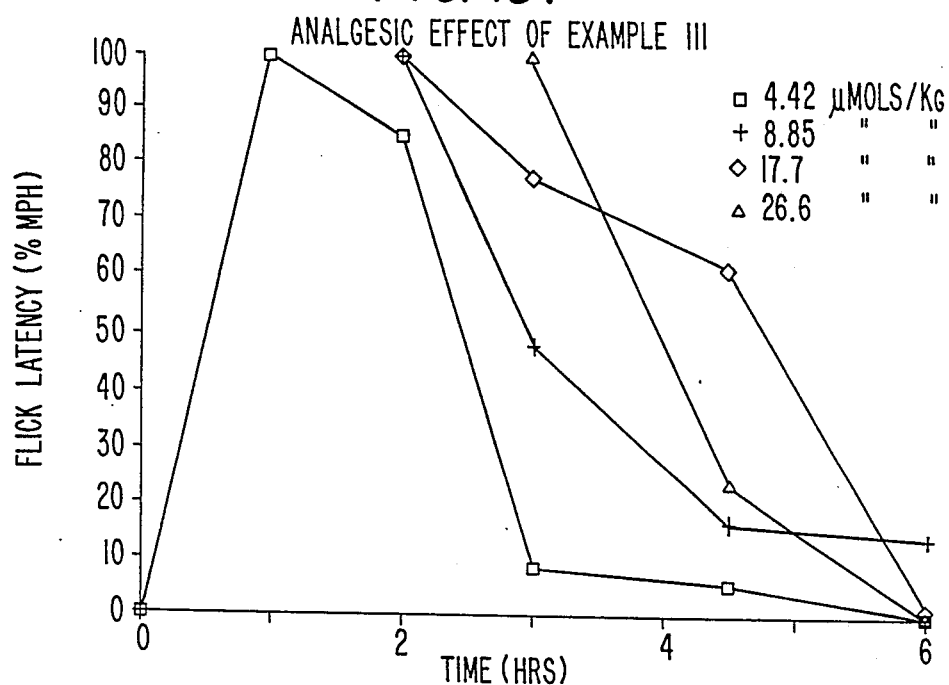
FIG. 15. ANALGESIC EFFECT OF EXAMPLE III
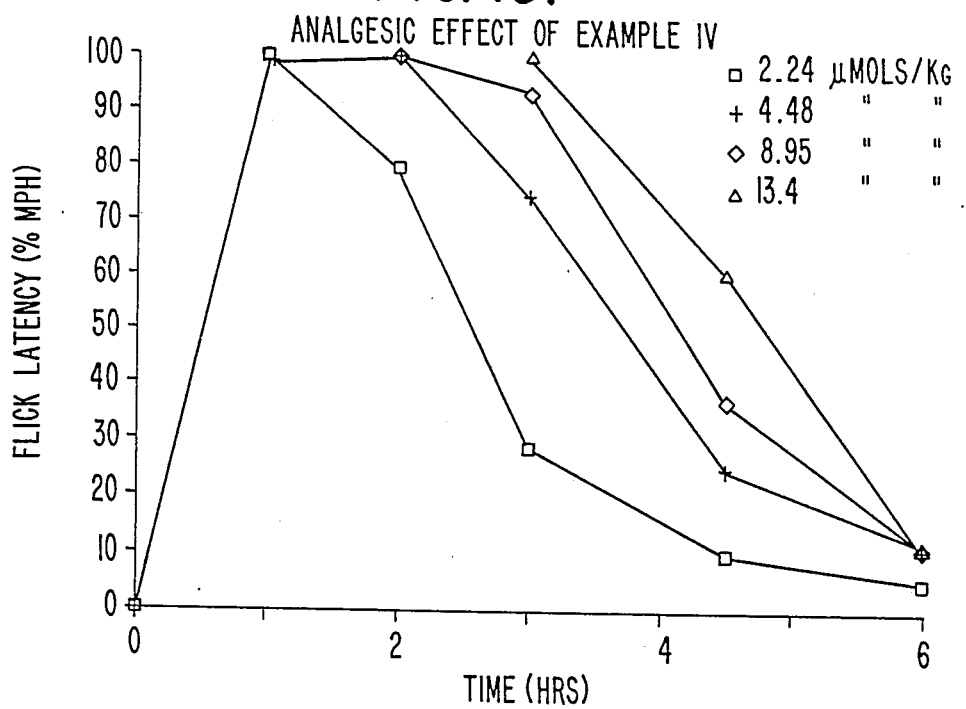
FIG. 16. ANALGESIC EFFECT OF EXAMPLE IV

ANALGESIC EFFECT OF MORPHINE

EXAMPLE XI
ANTAGONISM OF MORPHINE-INDUCED ANALGESIA

EXAMPLE XII
ANTAGONISM OF MORPHINE-INDUCED ANALGESIA

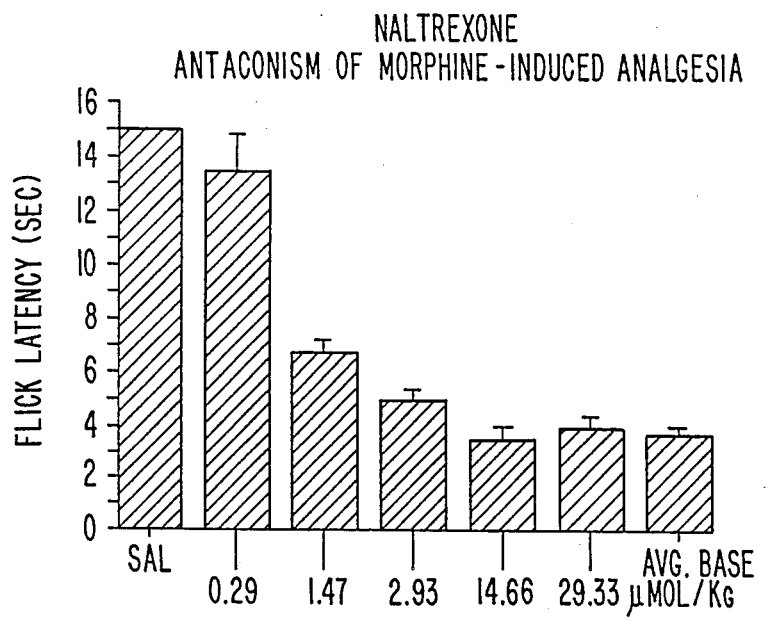
FIG. 20. NALTREXONE ANTAGONISM OF MORPHINE-INDUCED ANALGESIA
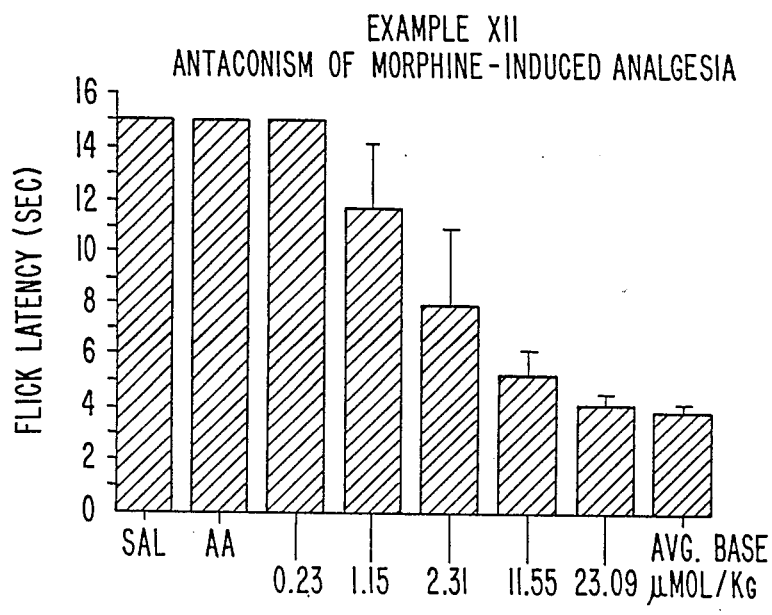
FIG. 21. EXAMPLE XII ANTAGONISM OF MORPHINE-INDUCED ANALGESIA

NALTREXONE EFFECTS ON FOOD INTAKE

EXAMPLE XII
EFFECTS ON FOOD INTAKE

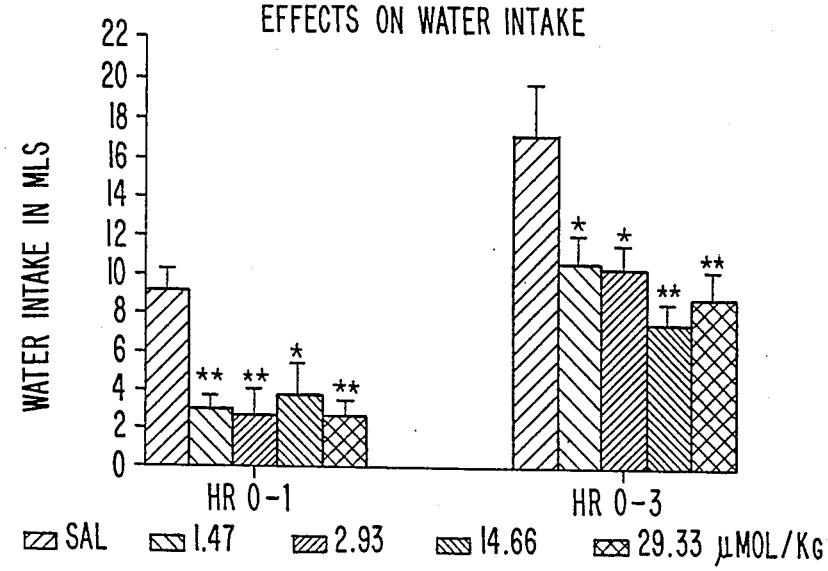
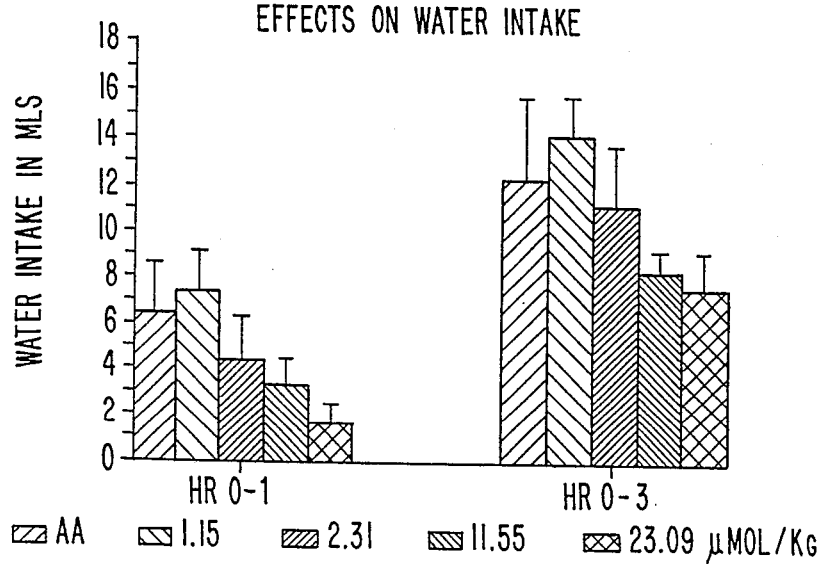

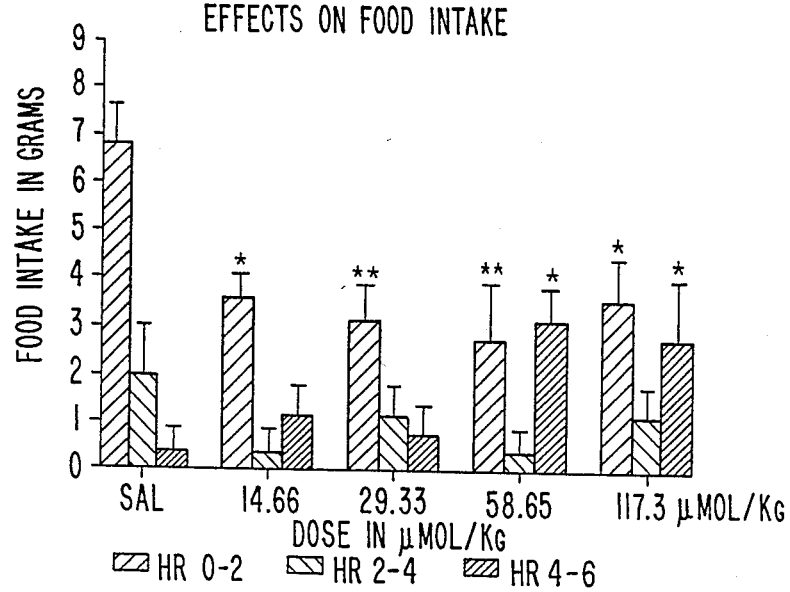
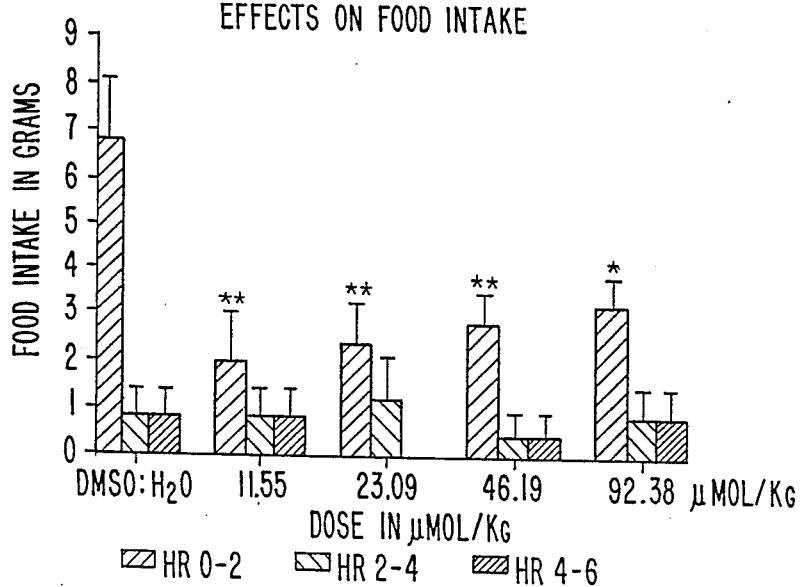

EXAMPLE XII
CONDITIONED TASTE AVERSION

EXAMPLE XII
CONDITIONED TASTE AVERSION

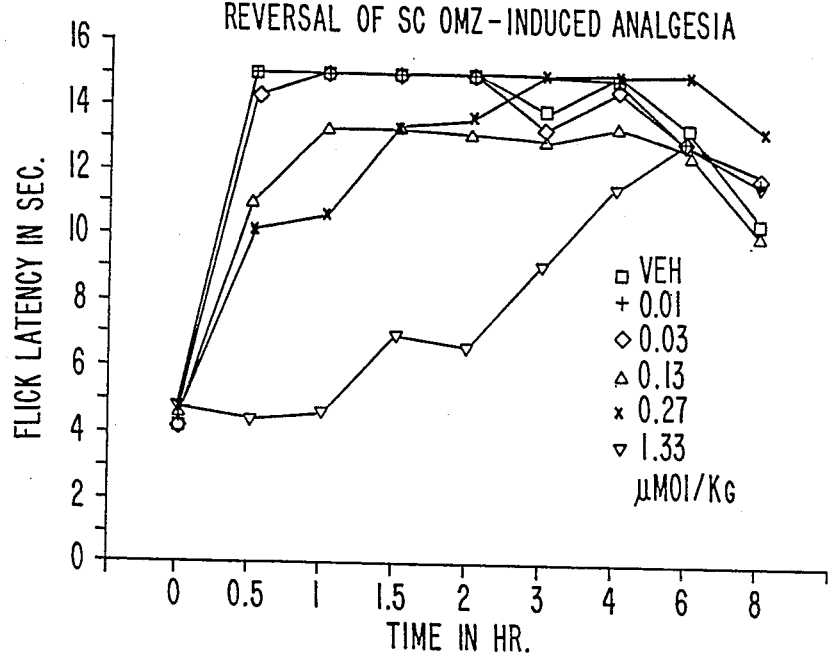
FIG. 30. NALTREXONE (SC) REVERSAL OF SC OMZ-INDUCED ANALGESIA
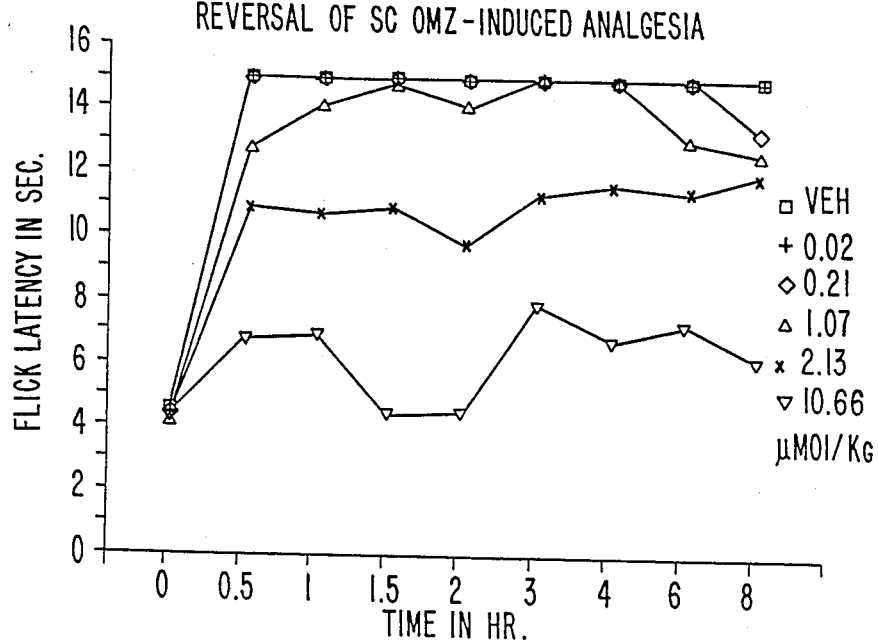
FIG. 31. EXAMPLE XII (SC) REVERSAL OF SC OMZ-INDUCED ANALGESIA

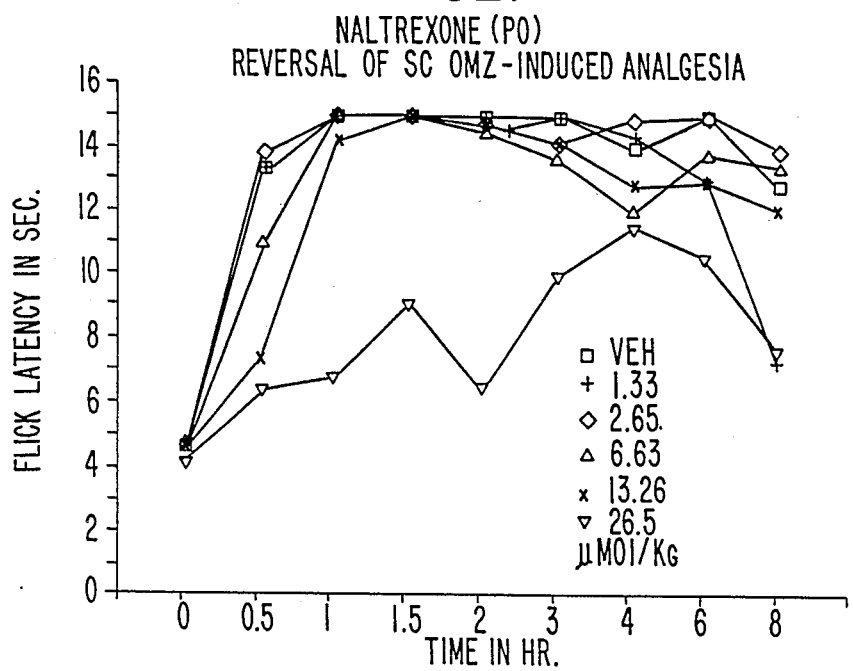
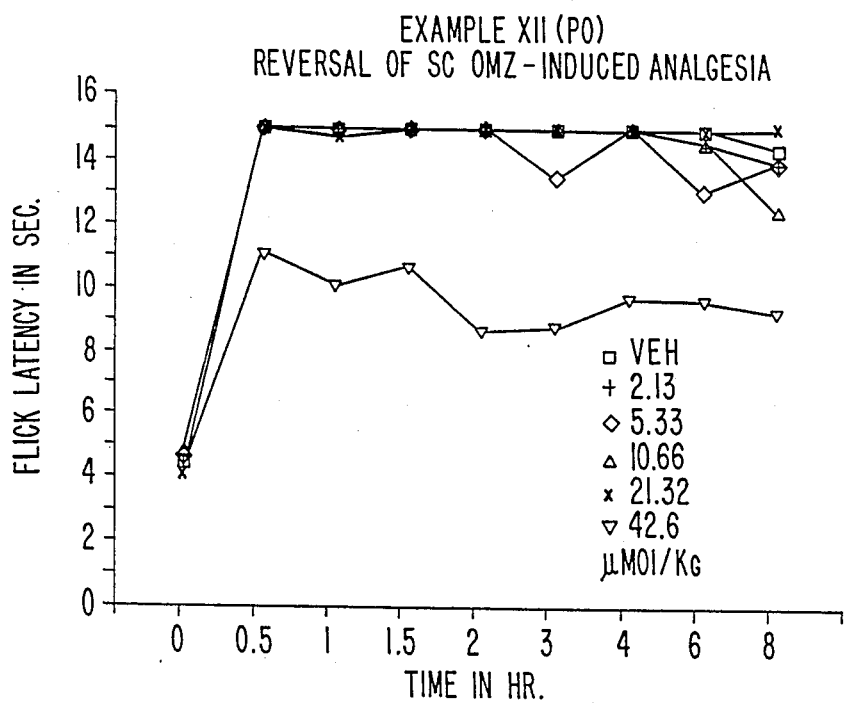

OXIMES OF OXYMORPHONE, NALTREXONE AND NALOXONE AS POTENT, SELECTIVE OPIOID RECEPTOR AGONISTS AND ANTAGONISTS

BACKGROUND OF THE INVENTION

1. Field of the Invention

The present invention pertains to novel long-acting analgesics, prophylactic or rescue agents in the treatment of opiate drug abuse and a new class of antiobesity drugs. In particular, the invention is directed to O-aryl or O-aralkyl ethers of oxymorphone, naltrexone and naloxone derived oximes, their pharmaceutically acceptable salts and to the methods of synthesizing the same.

2. Description Of The Prior Art

The evidence for multiplicity of opioid receptor subtypes in the prior art lead to the discovery of novel selective agonists and antagonists as reported in Lever et al. *Ann. Rep. Med. Chem.*, 18, 51 (1983). The discovery of a potent, selective agonist or antagonist reduces or eliminates the side effects associated with a nonselective compound. Increased potency and selectivity of the agonist and antagonist compounds generally results in a reduction of overall toxicity since less compound is generally required. Thus, in the case of analgesics, morphine and related opiates exhibit deleterious side effects such as respiratory depression, mood changes, and decreased intestinal motility with concomitant constipation, nausea, vomiting and alterations in the endocrine and autonomic nervous systems. Opiate antagonists in the prior art have been reported to show as side effects endocrine and gastrointestinal disturbance. The novel compounds of the present invention are improved over prior art opiate compounds in potency and selectivity as opioid receptor agonists and antagonists and in reducing or being substantially free of reported side effects of prior art opiate compounds.

Considerable evidence from radioligand binding studies in the prior art supports the existence of mu, delta, kappa and sigma opioid receptors [Simone et al. and in *Opioids-Past, Present and Future*, Tylor and Francis, London, pp 33–52, (1984) and Martin et al. *J. Pharmacol. Exp. Therap.* 196, 66 (1976)]. The mu-receptor was originally believed to be involved in the production of both analgesic and respiratory depressant effects. A more recent study suggests that one subclass of that receptor ($mu_1$) is responsible for the former and the other ($mu_2$) for the latter [Spiegel et al. *J. Pharmacol. Exp. Therap.* 228, 414 (1984)]. Subsequently the original group of investigators (Simone et al. *Life Sci.* in press (1985)) reported inhibition of overnight feeding by a $mu_1$-selective antagonist, naloxonazine.

The novel compounds of the present invention were the product of an extensive research investigation into the possible relationship between the hydrophobic bonding region present in the vicinity of the C-6 position of the opiate molecule when bound to the mu-receptor. The existence of the hydrophobic bonding region was clearly demonstrated by Pasternak et al. *J. Med. Chem.* 23, 674 (1980) in studies using the dimeric azines and the phenyl-hydrazones (Hahn et al. *J. Pharmacol. Exp. Therap.* in press (1985)). The ease of formation of oximes in the 14-hydroxy dihydromorphinone series has been the subject of a number of prior art references the most pertinent of which are believed to be Lewenstein et al. U.S. Pat. No. 3,320,262; Sawa et al. *Tetrahedron*, 24, 6185 (1968); Ko et al. *J. Med. Chem.* 27, 1727 (1984). The two known groups of oximes tested in the past were esters of carboxymethyl oximes [Lowenstein et al. U.S. Pat. No. 3,320,262] and oximes and their O-methyl ethers of oxymorphone, naloxone and naltrexone [Ko et al. *J. Med. Chem.* 27, 1727, (1984)].

In U.S. Pat. No. 3,320,262 only one compound, N-cyclopropylmethyl-nor-14-hydroxydihydrocodeinone-6-carboxymethyl methyl ester was examined in morphine dependent monkeys. At dosages of 1 and 2 mg/kg of body weight only, "partial suppression of symptoms was obtained" (Col. 6, ls. 67–71 of the patent). In the Ko et al. study the oximes and their O-methyl ethers of oxymorphone, naloxone and naltrexone were reported as less potent than parent ketones.

The unusually high potency and selectivity exhibited by the novel compounds of the invention is not disclosed or suggested in the available prior art. The novel and unexpected advantages of the potent selective opioid receptor agonists and antagonists over the prior art are further illustrated in the accompanying drawings together with the summary of the invention.

SUMMARY OF THE INVENTION

The present invention provides a potent, selective opioid receptor agonist or antagonist having the general formula:

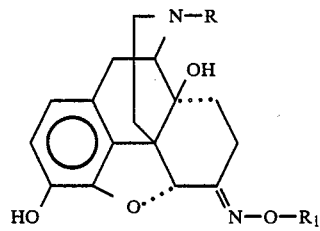

wherein R is cyclopropylmethyl, allyl or methyl, and $R_1$ is an unsubstituted or substituted aryl, aralkyl, heteroaryl, heteroaralkyl or a cycloalkyl group, with or without a heteroatom like S,O,N; and the pharmaceutically acceptable salts thereof.

DESCRIPTION OF THE DRAWINGS

Other advantages of the invention will become apparent to those skilled in the art from the following detailed description of the invention in conjunction with the accompanying drawings in which:

FIG. 1 is a graph illustrating representative inhibition of specific [$^3$H]DAGO ([$^3$H]-[D-Ala$^2$-MePhe$^4$-Glyol$^5$]-enkephalin) or [$^3$H]DADLE ([$^3$H]-[D-Ala$^2$-D-Leu$^5$]-enkephalin) binding to rat brain membranes of 6-Methyloximino-17-methyl-4,5α-epoxy-3, 14-dihydroxymorphinan (compound II of Example II);

FIG. 2 is a graph illustrating representative inhibition of specific [$^3$H]DAGO or [$^3$H]DADLE binding to rat brain membranes of 6-Methyloximino-17-cyclopropylmethyl-4,5α-epoxy-3, 14-dihydroxymorphinan (compound X of Exaple X);

FIG. 3 is a graph illustrating representative inhibition of specific [$^3$H]DAGO or [$^3$H]DADLE binding to rat brain membranes of 6-Benzyloximino-17-methyl-4,5α-epoxy-3, 14-dihydroxymorphinan (compound III of Example III);

FIG. 4 is a graph illustrating representative inhibition of specific [³H]DAGO or [³H]DADLE binding to rat brain membranes of 6-Benzyloximino-17-cyclopropylmethyl-4,5α-epoxy-3, 14-dihydroxymorphinan (compound XI of Example XI);

FIG. 5 is a graph illustrating representative inhibition of specific [³H]DAGO or [³H]DADLE binding to rat brain membranes of 6-Phenyloximino-17-methyl-4,5α-epoxy-3, 14-dihydroxymorphinan (compound IV of Example IV);

FIG. 6 is a graph illustrating representative inhibition of specific [³H]DAGO or [³H]DADLE binding to rat brain membranes of 6-Phenyloximino-17-cyclopropylmethyl-4,5α-epoxy-3, 14-dihydroxymorphinan (compound XII of Example XII);

FIG. 7 is a graph illustrating the reversibility of inhibition of [³H]DADLE binding as a result of pretreatment of rat forebrain membranes with naltrexone, 6-Methyloximino-17-cyclopropylmethyl-4,5α-epoxy-3, 14-dihydoxymorphinan (compound X of Example X), 6-Oximino-17-cyclopropylmethyl-4,5α-epoxy-3, 14-dihydroxymorphinan (compound IX of Example IX) and 6-Phenyloximino-17-cyclopropylmethyl -4,5α-epoxy-3, 14-dihydroxymorphinan (compound XII of Example IXX);

FIG. 8 is a graph illustrating the reversibility of inhibition of [³H]DADLE binding as a result of pretreatment of rat forebrain membranes with oxymorphone, 6-Methyloximino17-methyl-4,5α-epoxy-3, 14-dihydroxymorphinan (compound II of Example II), and 6-Phenyloximino-17-methyl 4,5α-epoxy-3, 14-dihydroxymorphinan (compound IV of Example IV);

FIG. 9 is a graph illustrating the reversibility of inhibition of [³H]DAGO binding as a result of pretreatment of rat forebrain membranes with naltrexone, 6-Methyloximino-17-cyclopropylmethyl-4,5α-epoxy-3, 14-dihydroxymorphina (compound X of Example X), 6-Oximino-17-cyclopropylmethyl-4,5α-epoxy-3, 14-dihydroxymorphinan (compound IX of Example IX) and 6-Phenyloximino-17-cyclopropylmethyl-4,5α-epoxy-3, 14-dihydroxymorphinan (compound XII of Example XII);

FIG. 10 is a graph illustrating the reversibility of inhibition of [³H]DAGO binding as a result of pretreatment of rat forebrain membranes with oxymorphone, 6-Methyloximino-17-methyl-4,5α-epoxy-3, 14-dihydroxymorphinan (compound II of Example II) and 6-Phenyloximino-17-methyl-4,5α-epoxy-3, 14-dihydroxymorphinan (compound IV of Example IV);

FIG. 11 is a graph illustrating the analgesic effect of 6-Benzyloximino-17-methyl-4,5α-epoxy-3, 14-dihydroxymorphinan (compound III of Example III) on tail flick latency in rats;

FIG. 12 is a graph illustrating the analgesic effect of 6-Phenyloximino-17-methyl-4,5α-epoxy-3, 14-dihydroxymorphinan (compound IV of Example IV) on tail flick latency in rats;

FIG. 13 is a graph illustrating the analgesic effect of morphine on tail flick latency in rats;

FIG. 14 is a graph illustrating the dose-response relationship for production of increased tail flick latency in rats by the administration of 6-Benzyloximino-17-methyl-4,5α-epoxy-3, 14-dihydroxymorphinan (compound III of Example III), 6-Phenyloximino-17-methyl-4,5α-epoxy-3, 14-dihydroxymorphinan (compound IV of Example IV) and morphine;

FIG. 15 is a graph illustrating the analgesic effect of 6-Benzyloximino-17-methyl-4,5α-epoxy-3, 14-dihydroxymorphinan (compound III of Example III) on tail flick latency in rats;

FIG. 16 is a graph illustrating the analgesic effect of 6-Phenyloximino-17-methyl-4,5α-epoxy-3, 14-dihydroxymorphinan (compound IV of Example IV) on tail flick latency in rats;

FIG. 20 is a graph illustrating the antagonism effect of naltrexone on morphine - induced analgesia in rats;

FIG. 21 is a graph illustrating the antagonism effect of 6-Phenyloximino-17-cyclopropylmethyl-4,5α-epoxy-3, 14-dihydroxymorphinan (compound of XII Example XII) morphine induced analgesia in rats;

FIG. 24 is a graph illustrating the effect of naltrexone on the water intake in 24 hour food deprived rats;

FIG. 25 is a graph illustrating the effect of 6-Phenyloximino-17-cyclopropylmethyl-4,5α-epoxy-3, 14-dihydroxymorphinan (compound XII of Example XII) on the food intake in 24 hour food deprived rats;

FIG. 26 is a graph illustrating the time course of the effects of naltrexone on the food intake in 24 hours food deprived rats;

FIG. 27 is a graph illuetrating the time course of the effects of 6-Phenyloximino-17-cyclopropylmethyl-4,5α-epoxy-3, 14-dihydroxymorphinan (compound XII of Example XII) on the food intake in 24 hour food deprived rats;

FIG. 30 is a graph illustrating the time course of the antagonism by naltrexone of oxymorphonazine (OMZ)-induced analgesia in rats following SC administration;

FIG. 31 is a graph illustrating the time course of the antagonism by 6-Phenyloximino-17-cyclopropylmethyl-4,5α-epoxy-3, 14- dihydroxymorphinan (compound XII of Example XII) of oxymorphonazine (OMZ)-induced analgesia in rats following SC administration;

FIG. 32 is a graph illustrating the time course of the antagonism by naltrexone of OMZ-induced analgesia in rats following PO administration; and FIG. 33 is a graph illustrating the time course of the antagonism by 6-Phenyloximino-17-cyclopropylmetyl-4,5α-epoxy-3, 14-dihydroxymorphinan (compound XII of Example XII) of OMZ-induced analgesia in rates following PO administration.

DETAILED DESCRIPTION OF THE INVENTION

Figure 17:
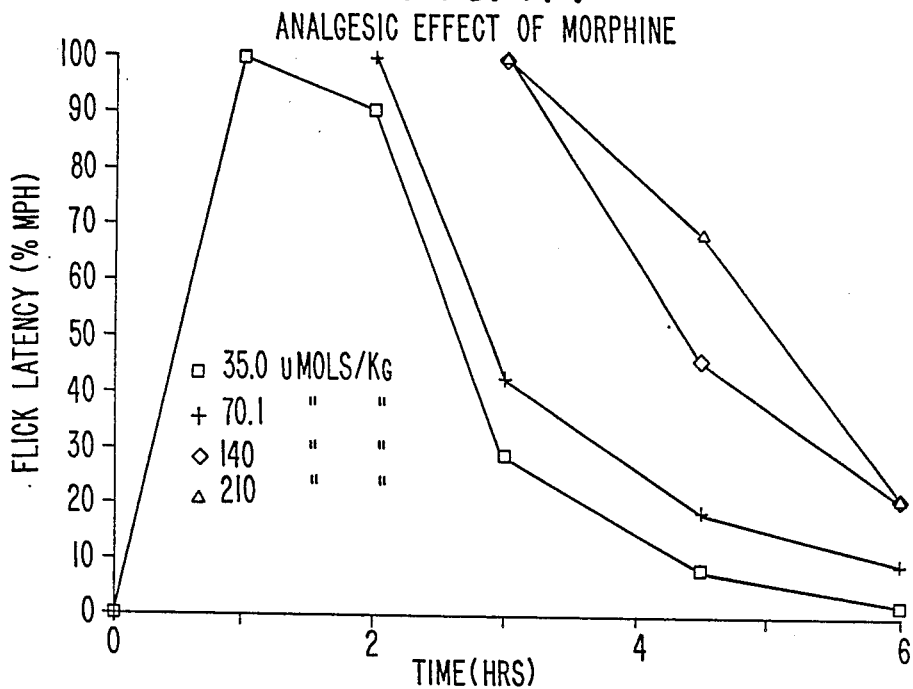
FIG. 17 is a graph illustrating the analgesic effect of morphine on tail flick latency in rats.

The structure and formulation of the novel compounds of the invention was based upon the presence of a hydrophobic bonding region in the vicinity of the C-6 position of an opiate agonist or antagonist when complexed with mu-receptor. It is possible this region might be absent or have different dimensions in other opioid receptor types than the mu opioid receptors. The structure of the novel compounds, which contain the hydrophobic bonding region in the vicinity of the C-6 position, provides potent compounds having higher affinity towards a mu-receptor than towards other classes of opioid receptors, rendering them selective. This would therefore permit one to selectively stimulate or antagonize (depending on the compound used) the mu-receptor in tissue also containing other opioid receptors. As a result of the greater affinity and selectivity of the present invention fewer side effects are exhibited by the novel compounds.

The high affinity and selectivity of such compounds, e.g.: 6-phenyl or 6-benzyloximino-4, 5α-epoxy-17-cyclopropylmethyl-3, 14-dihydroxymorphinan, has been demonstrated in receptor binding studies and in rats by their ability to provide a long lasting inhibition of morphine-induced analgesia. The analgesic effects of such compounds, e.g.: 6-phenyl or 6-benzyloximino-4,5α-epoxy-17-methyl-3, 14-dihydroxymorphinan, have been demonstrated in rats by utilizing tail flick latencies. The appetite suppression of such compounds, e.g.: 6-phenyl or 6-benzyloximino-4, 5α-epoxy-17-cyclopropylmethyl-3, 14-dihydroxymorphinan has been demonstrated by a long lasting inhibition of food intake in schedule-adapted food deprived rats.

The novel compounds of the invention can be readily prepared by the reaction of an appropriate ketone, e.g. 17-allyl-4,5α-epoxy-3, 14-dihydroxymorphinan-6-one, with the O-aryl or O-aralkyl hydroxylamines. The aryl or aralkyl may be but is not limited to, for example, phenyl; substituted phenyl wherein the substituent is halogen, hydroxy, nitro, methoxy, methyl, trifluoromethyl, amino, etc.; naphthyl; tetrahydronaphthyl; heterocycle, for example 4- or 5-benzimidazolyl; or, benzyl, substituted benzyl, phenethyl and the like.

The preparation of compounds for administration in pharmaceutical preparations may be in a variety of well known methods known to those skilled in the art of pharmacy. More specifically the novel compounds may be formulated as an acid salt, i.e., HCl salt, sulfate, phosphate, nitrate methanesulfonate, tartrate and other pharmaceutically acceptable salts and compositions.

In parenteral administration of the novel compounds and compositions of the invention the compounds may be presented in aqueous injection solutions which may contain antioxidants, buffers, bacteriostats, etc. Extemporaneous injection solutions may be prepared from sterile pills, granules or tablets which may contain diluents, dispersing and surface active agents, binders and lubricants.

In the case of oral administration, fine powders or granules of the compound may be formulated with diluents and dispersing and surface active agents, and may be prepared in a draft in water or in a syrup, in capsules or cachets in the dry state or in a non-aqueous suspension, when a suspending agent may be included. The compounds may also be administered in tablet form along with optional binders and lubricants, or in a suspension in water or a syrup or an oil or in a water/oil emulsion and may include flavoring, preserving, suspending, thickening and emulsifying agents. The granules or tablets for oral administration may be coated and other pharmaceutically acceptable agents and formulations may be utilized as known to those skilled in the art.

The following examples are illustrative of compounds of the invention but are not to be construed as limiting the invention thereto.

EXAMPLES

PREPARATION EXAMPLES

EXAMPLE I

6-Oximino-17-methyl-4,5α-epoxy-3,14-dihydroxymorphinan

A solution of oxymorphone (1.2 g, 4 mmol) and hydroxylamine hydrochloride (0.35 g, 5 mmol) in 20 mL of methanol was treated with 2 mL of 10% aqueous NaOH and stirred at room temperature for 15 h. The reaction mixture was poured into water and extracted with 150 mL $CHCl_3$ (3×50 mL). The $CHCl_3$ extract was dried ($MgSO_4$), and evaporated. The residue was recrystallized from THF-petroleum ether yielding 600 mg (47.4%), mp 270°–71° C. IR: (KBr): No C=O absorption at 1720 $cm^{-1}$. H NMR ($d_6$DMSO) δ 4.83 (s, $C_5H$), Rf: silica gel EtOAc-EtOH-$NH_4OH$ (100:1:1) 0.18. Anal. Calcd for $C_{17}H_{20}N_2O_4$C, 64.54; H, 6.37; N, 8.86. Found C, 64.76; H, 6.5; N, 8.58.

EXAMPLE II

6-Methyloximino-17-methyl-4,5α-epoxy-3,14-dihydroxymorphinan

A solution of oxymorphone (0.9 g, 3 mmol) and O-methyl hydroxylamine hydrochloride (0.33 g, 3.9 mmol) in 15 mL MeOH containing 1.6 mL of 10% aqueous NaOH was refluxed for 5 h, cooled, diluted with water (approximately 100 mL) and extracted with 150 mL $CHCl_3$ (3×50 mL). The combined extracts were dried ($MgSO_4$), and evaporated. The residue obtained was recrystallized from $CH_2Cl_2$-hexane to yield 0.84 g on the product. It was further purified by flash column chromatography on silica gel, eluting with EtOAc-EtOH-$NH_4OH$ (100:1:1) (approx. size 40 microns). The combined fractions were evaporated in vacuo and the residue obtained was recrystallized from hexane-petroleum ether. Yield: 0.4 g (40%). mp 115°–116° C. IR: (KBr): No C=O absorption at 1730 $cm^{-1}$. H NMR ($CDCl_3$)δ4.92 (s,$C_5H$), 3.85 (s, $OCH_3$) Rf: silica gel 60 in EtOAc-EtOH-$NH_4OH$ (100:1:1) 0.30. Anal. Calcd for: $C_{18}H_{22}N_2O_4$: C, 65.44; H, 6.71; N, 8.48. Found: C, 65.51; H, 6.74; N, 8.46.

EXAMPLE III

6-Benzyloximino-17-methyl-4,5α-epoxy-3,14-dihydroxymorphinan

Oxymorphone (1.0 g, 3.3 mmol) was dissolved in 20 mL of 95% EtOH containing con-HCl (1 mL). O-Benzylhydroxylamine hydrochloride (0.6 g, 3.75 mmol) was added and the mixture dissolved by warming for a few minutes. Stirring continued for 15 h at room temperature and then the solvent was removed under reduced pressure. The residue was dissolved in water, made alkaline with 5% aqueous $NaHCO_3$ and extracted with 200 mL (4×50 mL) $CHCl_3$. The $CHCl_3$ extract was dried ($MgSO_4$) and evaporated. The residue obtained was chromatographed on silica gel column (approx. size 40 microns) with CHCl3-MeOH (95:5) mixture as eluent. The combined fractions were evaporated in vacuo, the residue dissolved in EtOH, and acidified with conc. HCl. Evaporation of the solvent gave 0.4 g (27%) of the product. mp>150° C. (decomp); IR: (KBr): No absorption for C=O at 1730 cm$^{-1}$; $^1$H NMR (d$_6$DMSO):δ7.2 (s,C$_6$H$_5$). TLC: Rf: silica gel 60 in CHCl$_3$-MeOH-NH$_4$OH (90:10:1) 0.65. Anal. Calcd for: C$_{24}$H$_{27}$N$_2$ClO$_4$. ½ H$_2$O: C, 63.78; H, 6.24; N, 6.20; Cl, 7.84. Found: C, 63.84; H, 6.30; N, 6.17; Cl, 7.83.

EXAMPLE IV

6-Phenyloximino-17-methyl-4,5α-epoxy-3,14-dihydroxymorphinan

A mixture of oxymorphone (1 g, 3.3 mmol) and O-phenylhydroxylamine hydrochloride (0.6 g, 4 mmol) in 20 mL of 95% EtOH, was acidified with conc. HCl (1 mL) and stirred for two days. The crystallized product was filtered and collected (1.1 g). The salt was dissolved in water, the solution made alkaline with 5% aqueous NaHCO$_3$ and extracted with 200 mL (4×50 mL) CHCl$_3$. The CHCl$_3$ extract was dried (MgSO$_4$), and evaporated. The residue obtained was chromatographed on a column of silica gel (approx. size 40 microns) with CHCl$_3$-MeOH (94:6). The combined fractions were evaporated in vacuo, the residue dissolved in EtOH, acidified with conc. HCl and concentrated. Dilution with ether precipitated the compound which was filtered and dried. Yield 0.4 g (27%). mp>140° C. (decomp); IR: (KBr): No C=O absorption at 1730 cm$^{-1}$; $^1$H NMR (d$_6$DMSO). δ7.3 (m,C$_6$H$_5$). Rf: silica gel 60 in CHCl$_3$-MeOH-NH$_4$OH (90:10:1) 0.75. Anal. Calcd for C$_{23}$H$_{24}$N$_2$O$_4$.HCl.H$_2$O: C, 61.81; H, 6.09; N, 6.27; Cl, 7.93. Found: C, 62.04; H, 6.17; N, 6.19; Cl, 7.87.

EXAMPLE V

6-Oximino-17-allyl-4,5α-epoxy-3,14-dihydroxymorphinan

A mixture of naloxone hydrochloride (1.085 g, 3 mmol) and hydroxylamine hydrochloride (0.28 g, 4 mmol) was taken up in 30 mL of MeOH containing 2.8 mL of 10% aqueous NaOH. The mixture was stirred at room temperature for 24 h. Water was added (100 mL), and the oxime extracted into CHCl$_3$ (3×50 mL). The extract was dried (MgSO$_4$), and the solvent evaporated. The residue obtained was recrystallized from CH$_2$Cl$_2$-petroleum ether. Yield: 840 mg (81.8%); mp: 119° C. IR: (KBr): No C=O absorption at 1717 cm$^{-1}$. $^1$H NMR (CDCl$_3$) δ4.98 (s,C$_5$H); Rf: silica gel 60 in EtOAc-EtOH-NH$_4$OH (100:1:1) 0.13. Anal. Calcd for: C$_{19}$H$_{22}$N$_2$O$_4$: C, 66.65; H, 6.48; N, 8.18. Found: C, 66.70; H, 6.52; N, 8.08.

EXAMPLE VI

6-Methyloximino-17-allyl-4,5α-epoxy-3,14-dihydroxymorphinan

A solution of naloxone hydrochloride (1.09 g, 3 mmol) and O-methylhydroxylamine hydrochloride (0.33 g, 3.9 mmol) in 15 mL MeOH was stirred overnight. After the addition of 3.2 mL of 10% aqueous NaOH, the mixture was refluxed for 5 h. It was cooled, diluted with approx. 100 mL of water, and extracted with 150 mL CHCl$_3$ (3×50 mL). The combined extracts were dried (MgSO$_4$) and evaporated. The residue obtained was recrystallized from hexane-petroleum ether. Yield 0.8 g, (75%) mp 128–129° C. IR (KBr): No C=O absorption at 1717 cm$^{-1}$; H NMR (CDCl$_3$): δ4.95 (s, C$_5$H), 3.82 (s, OCH$_3$). Rf: silica gel 60 in EtOAc-EtOH-NH$_4$OH (100:1:1) 0.50. Anal. Calcd for C$_{20}$H$_{24}$N$_2$O$_4$: C, 67.40; H, 6.79; N, 7.86. Found: C, 67.27; H, 6.84; N, 7.82.

EXAMPLE VII

6-Benzyloximino-17-allyl-4,5α-epoxy-3,14-dihydroxymorphinan

A mixture of naloxone hydrochloride (0.723 g, 2 mmol) and O-benzylhydroxylamine hydrochloride (0.32 g, 2 mmol) in 20 mL of 95% EtOH containing 0.1 mL of conc.HCl was stirred for 15 h at room temperature. The solvent was evaporated under reduced pressure and the residue dissolved in water. The solution was made alkaline with 5% aqueous NaHCO$_3$ and extracted with 100 mL (4× 25) of CHCl$_3$. The CHCl$_3$ extract was dried (MgSO$_4$), and evaporated. The residue was chromatographed on a column of silica gel (approx. 40 micron size) with ethyl acetate-toluene mixture (1:1) as eluent. The combined fractions were evaporated in vacuo, the residue dissolved in EtOH, acidified with conc. HCl. and evaporated to dryness. Yield: 0.375 g (40%); mp>150° C. (decomp); IR (KBr): No C=O absorption at 1717 cm$^{-1}$; $^1$H NMR (d$_6$DMSO-D$_2$O): δ8.00 (s,C$_6$H$_5$). Rf: silica gel 60 in CHCl$_3$-MeOH-NH$_4$OH (90:10:1) 0.65. Anal. Calcd for C$_{26}$H$_{29}$N$_2$ClO$_4$: C, 66.59; H, 6.23; N, 5.97; Cl, 7.56. Found: C, 66.65; H, 6.43; N, 5.86; Cl, 7.75.

EXAMPLE VIII

6-Phenyloximino-17-allyl-4,5α-epoxy-3,14-dihydroxymorphinan

A mixture of naloxone hydrochloride (0.723 g, 2 mmol) and O-phenylhydroxylamine hydrochloride (0.3 g, 2 mmol) was dissolved in 20 mL 95% EtOH, and stirred for 2 days at room temperature. The reaction mixture was poured into 250 mL of ether and the precipitated product was collected by filtration. The compound was dissolved in water, the solution made alkaline with 5% aqueous NaHCO$_3$ and extracted with 150 mL (3×50) of CHCl$_3$. The CHCl$_3$ extract was dried (MgSO$_4$) and evaporated. The residue obtained was chromatographed on a column of silica gel (approx. size 40 microns) with ethyl acetate-toluene mixture (1:1) as eluent. The combined fractions were evaporated in vacuo, the residue dissolved in ethanol, acidified with conc. HCl and concentrated. Addition of ether precipitated the compound, which was collected by filtration and dried (MgSO$_4$). Yield: 0.55 g (60.5%); mp>180° C. (decomp); IR (KBr): No C=O absorption at 1730 cm$^{-1}$. $^1$H NMR (d$_6$DMSO). δ7.15 (m, C$_6$H$_5$). Rf: silica gel in ethyl acetate - toluene (1:1) 0.42. Anal. Calcd for C$_{25}$H$_{27}$N$_2$ClO$_4$: C, 66.00; H, 5.98; N, 6.16; Cl, 7.79. Found: C, 65.63; H, 6.03; N, 5.92; Cl, 7.70.

EXAMPLE IX

6-Oximino-17-cyclopropylmethyl-4,5α-epoxy-3,14-dihydroxymorphinan

A mixture of naltrexone hydrochloride (1.34 g, 3 mmol) and hydroxylamine hydrochloride (0.28 g, 4 mmol) was dissolved in 20 mL of MeOH and 2.8 mL of aqueous NaOH added. The mixture was stirred for 15 h. Water was added (100 mL) and the mixture extracted with 150 mL CHCl$_3$ (3×50 mL). The combined extracts were dried (MgSO$_4$) and evaporated. The residue obtained was chromatographed on a column of silica gel (approx. size 40 microns) using ethyl acetate-ethanol-NH$_4$OH (300:1.5:2) as eluent. The combined fractions were evaporated and the residue recrystallized from CH$_2$Cl$_2$-petroleum ether. Yield: 0.54 g (50.5%) mp 235–236° C. IR (KBr): No C=O absorption at 1720 cm$^{-1}$. $^1$H NMR (CDCl$_3$) δ6.7 (2d, 2H, J=10 Hz) 5 (s,C$_5$H); Rf: silica gel 60 in ethylacetate-EtOH-NH$_4$OH (100:1:1) 0.22. Anal. Calcd for C$_{20}$H$_{24}$N$_2$O$_4$: C, 67.40; H, 6.79; N, 7.86. Found: C, 67.12; H, 6.88; N, 7.63.

EXAMPLE X

6-Methyloximino-17-cyclopropylmethyl-4,5α-epoxy-3,14-dihydroxymorphinan

Naltrexone hydrochloride (1.134 g, 3 mmol) was added to a solution of CH$_3$ONH$_2$HCl (0.33 g, 3.9 mmol) in 15 mL MeOH containing 3.2 mL 10% aqueous NaOH. The mixture was refluxed for 5 h, cooled, diluted with approximately 100 mL H$_2$O and extracted with 150 mL CHCl$_3$ (3×50 mL). The combined CHCl$_3$ extracts were dried (MgSO$_4$) and evaporated. TLC showed that the reaction was incomplete and hence the reaction was repeated as before using the mixture, CH$_3$ONH$_2$HCl (0.165 g, 1.9 mmol) and 0.8 mL of 10% aqueous NaOH. After workup the product was chromatographed on a column of silica gel (approx. size 40 microns) using EtOAC-EtOH-NH$_4$OH (100:1:0.5) as eluent. The fractions were combined, evaporated and the residue recrystallized from hexane-petroleum ether. Yield: 0.55 g (49.6%). mp 172°–173° C. IR (KBr): No C=O absorption at 1720 cm$^{-1}$; $^1$H NMR: (CDCl$_3$)δ4.95 (s, C$_5$H), 3.82 (s, OCH$_3$); Rf: silica gel 60 in EtOAc-EtOH-NH$_4$OH (100:1:1) 0.40. Anal. Calcd for C$_{21}$H$_{26}$N$_2$O$_4$: C, 68.09; H, 7.07; N, 7.56. Found: C, 67.96; H, 7.11; N, 7.55.

EXAMPLE XI

6-Benzyloximino-17-cyclopropylmethyl-4,5α-epoxy-3,14-dihydroxymorphinan

A mixture of naltrexone hydrochloride (0.755 g, 2 mmol) and O-benzylhydroxylamine hydrochloride (0.32 g, 2 mmol) in 20 mL of 95% EtOH containing 0.1 mL of conc. HCl was stirred for 15 h. at room temperature. The solvent was evaporated under reduced pressure and the residue dissolved in water. The solution was made alkaline with 5% aqueous NaHCO$_3$. The precipitated product was collected by filtration. The product was purified by chromatography using a silica gel (approx. 40 micron size) column with ethyl acetate-toluene (1:1) mixture as eluent. The combined fractions were evaporated in vacuo, the residue dissolved in EtOH, acidified with conc.HCl and evaporated to dryness. Yield: 0.29 g (30%) mp>200° C. (decomp); IR (KBr): No C=O absorption at 1720 cm$^{-1}$; $^1$H NMR (d$_6$DMSO-D$_2$O)δ7.8 (s, C$_6$H$_5$); Rf: silica gel in ethyl acetate-toluene (1:1) 0.35. Anal. Calcd for: C$_{27}$H$_{31}$N$_2$ClO$_4$. C, 67.14; H, 6.47; N, 5.80; Cl 7.34. Found: C, 66.86; H, 6.44; N, 5.68; Cl, 7.31.

EXAMPLE XII

6-Phenyloximino-17-cyclopropylmethyl-4,5α-epoxy-3,14-dihydroxymorphinan

A mixture of naltrexone hydrochloride (0.755 g, 2 mmol) and O-phenylhydroxylamine hydrochloride (0.30 g, 2 mmol) was dissolved in 20 mL of 95% EtOH and stirred for 2 days at room temperature. The reaction mixture was poured into 250 mL ether and the precipitated product was collected by filtration. The compound was dissolved in water, the solution made alkaline with 5% NaHCO$_3$, and extracted with 150 mL (3×50 mL) of CHCl$_3$. The CHCl$_3$ extract was dried (MgSO$_4$) and evaporated. The residue obtained was chromatographed on a silica gel (approx. size 40 microns) column with ethyl acetate-toluene (1:1) as eluent. The combined fractions were evaporated in vacuo, the residue dissolved in EtOH, acidified with conc. HCl. and evaporated to dryness. Yield: 0.34 g (36%); mp>150° C. (decomp); IR (KBr): No C=O absorption at 1720 cm$^{-1}$; $^1$H NMR (d$_6$DMSO): δ7.6 (m, C$_6$H$_5$). Rf: silica gel in ethyl acetate-toluene (1:1) 0.34. Anal. Calcd for C$_{26}$H$_{29}$N$_2$ClO$_4$: C, 66.59; H, 6.23; N, 5.97; Cl, 7.56. Found: C, 66.30; H, 6.21; N, 6.05; Cl, 7.31.

PHARMACOLOGICAL EVALUATION

The analgesic, appetite suppressant and opiate drug abuse treatment properties of the novel compounds were evaluated in vitro and in vivo employing pharmacologically accepted in vitro and in vivo tests as reported in the following Examples 13 to 17, the accompanying tables and drawings.

EXAMPLE XIII

The interaction of some of the novel compounds with mu- and delta-type opioid receptors present in brain membranes was examined in vitro. In accordance with the methods of Pert and Snyder (1978), the potency of compounds II–IV, and VI–XII to inhibit specific [$^3$H]DAGO (mu-type receptor) or [$^3$H]DADLE (delta-type receptor) was determined using rat forebrain membranes. Computer assisted analysis (EBDA) was used to determine apparent Ki values for the various compounds. Results are reported in the following Tables 1 and 2.

TABLE 1

POTENCY OF OXYMORPHONE AND ANALOGS TO INHIBIT SPECIFIC BINDING TO MU AND DELTA OPIOID RECEPTORS

| COMPOUND | Ligand | |
|---|---|---|
| | [$^3$H]DAGO Ki (nM) | [$^3$H]DADLE Ki (nM) |
| OXYMORPHONE | 1.6 ± 0.12 (0.77) | 20 ± 8.7 (0.44) |
| OXYMORPHONE-0-METHYLOXIME | 0.97 ± 0.10 (0.91) | 3.44 ± 0.83 (0.56) |
| OXYMORPHONE-0-BENZYLOXIME | 1.58 ± 0.07 (1.06) | 2.80 ± 1.6 (0.70) |
| OXYMORPHONE-0-PHENYLOXIME | 0.84 ± 0.09 (0.74) | 0.91 ± 0.10 (0.72) |

Values represent the MEAN±S.E.M. of the Ki(nM) for each compound to inhibit specific binding of the indicated ligand to rate brain membranes. The values are from two÷five separate experiments and were calculated according to the method of Cheng and Prusoff [Biochem. Pharmacol. 1973, 22, 3099–3108] together with the EBDA Program. Numbers in parentheses are the mean Hill coefficients for each compound to inhibit ligand binding.

TABLE 2
POTENCY OF NALTREXONE DERIVATIVES TO INHIBIT SPECIFIC LIGAND BINDING TO MU OR DELTA OPIOID RECEPTORS IN VITRO

| COMPOUND | Ligand [$^3$H]DAGO $K_i$ (nM) | [$^3$H]DADLE $K_i$ (nM) |
|---|---|---|
| NALTREXONE | 0.60 ± 0.10 (0.77) | 1.40 ± 1.00 (0.44) |
| NALTREXONE-METHYLOXIME | 0.66 ± 0.06 (0.97) | 1.80 ± 0.22 (0.72) |
| NALTREXONE BENZYLOXIME | 0.55 ± 0.12 (0.97) | 0.70 ± 0.22 (0.85) |
| NALTREXONE OXIME | 0.24 ± 0.03 (0.81) | N.D. |
| NALTREXONE PHENYLOXIME | 0.21 ± 0.08 (0.61) | 1.70 ± 0.51 (0.73) |

Values represent the MEAN ±S.E.M. of the $K_i$ (nM) for each compound to inhibit specific binding of the indicated ligand to rat brain membranes. The values are from two÷seven separate experiments and were calculated according to the method of Cheng and Prusoff together with the EBDA program. Numbers in parentheses are the mean Hill coefficients for each compound to inhibit ligand binding. N.D. = not determined Compounds prepared in Examples II-IV and VI$_3$–VII (not shown) showed little receptor-type selectivity to displace specifically bound [$^3$H] opiates from opiate receptors. Compounds in Examples IX and XII were 3-fold more potent than the compound in Example X or XI, or naltrexone, to inhibit specific [$^3$H]DAGO binding. Furthermore, compound in Example XII was ninefold more selective to inhibit binding at the site labeled by [$^3$H]DAGO than the site labeled [$^3$H]DADLE, whereas naltrexone was only 2.3-fold more selective.

Patterns of inhibition of ligand binding are shown in FIGS. 1-6. FIGS. 1-6 illustrate representative inhibition of specific [$^3$H]DAGO or [$^3$H]DADLE binding to rat brain membranes by analogs of oxymorphone or naltrexone. Compounds prepared in Examples II, III, VIII (not shown), and X displaced [$^3$H] opiate binding as expected (FIGS. 1, 2 and 3). In contrast, compounds XI (FIG. 4), IV, and XII (FIG. 6) appeared to continue to inhibit a percentage of ligand binding at very low drug concentrations.

Compounds as prepared in Examples II, X, IV, IX, XII as well as oxymorphone and naltrexone were examined for their ability to inhibit [$^3$H] opiate binding in a pseudo-irreversible manner (FIG. 7-10). In FIGS. 7-10 the effect of pretreatment of rat forebrain membranes with various compounds on the specific binding of [$^3$H]DAGO or [$^3$H]DADLE is illustrated. Rat forebrain membranes were incubated (30 min; 37°) in the presence of $10^{-8}$M of the indicated drug. Portions of the tissue were washed by centrifugation and resuspension in fresh buffer either 0, 1, 2 or 3 times prior to incubation with the radioligand. Control tissue was treated identically but was not exposed to any drug. The values represent the amount of specific binding observed in membranes following drug pretreatment and the indicated number of washes. The washes themselves did not affect ligand binding. In the FIGS. 7-10 the reported values are the means of three separate experiments. Following incubation (30 min; 37°) of brain membranes in the presence of $10^{-8}$M of the indicated drug, specific [$^3$H]DAGO and [$^3$H]DADLE binding was markedly decreased even after 3 washes of tissue(s), when the tissue had been exposed to compounds of Examples IV or XII. In contrast, binding of the ligand to tissue(s) previously exposed to compounds of Examples II or X did not differ significantly from the tissues exposed to oxymorphone or naltrexone, with complete specific binding being restored after 2-3 washes. The results indicate that compounds of Examples IV and XII, unlike oxymorphone and naltrexone, interact with opiate receptors in vitro in a pseudo-irreversible fashion.

EXAMPLE XIV

The analgesic properties of the compounds prepared in accordance with Examples III and IV were evaluated in rats using the radiant heat and tail flick paradigm. In the first experiment, rats were injected subcutaneously (S.C.) with one of four doses of the compound of Example III, IV or morphine as a comparison standard immediately following the determination of their baseline flick latencies, and flick latencies were determined at 30 min intervals through 3.5 hr. The doses were 1.11, 2.21, 3.32 or 4.43 μmole/kg for the compound of Example III; 0.56, 1.12, 2.24 or 3.36 μmole/kg for the compound of Example IV; and 3.52, 7.01, 10.5 or 14.0 μmole/kg for morphine. The results for the compounds of Example III, IV and morphine are shown in FIGS. 11, 12, and 13, respectively. Flick latencies in FIGS. 11-13 were determined at 30 minute intervals through 3.5 h and the data was expressed as a percentage of the maximum possible effect (% MPE). A 15 sec. cut-off latency was used to minimize tissue damage. The values shown are the mean values for 6 rats. The oximes are clearly more potent than morphine, with doses of 2.21 μmole/kg of the compound of Example III and 1.12 μmole/kg of the compound of Example IV for producing analgesia approximately equal to that of 10.5 μmole/kg of morphine.

In order to further quantify the differences in analgesic potency, rats were injected S.C. with one of four lower doses of the compounds immediately following the determination of their baseline flick latencies and flick latencies were determined 30 min later. Log dose-response curves for the compounds of Examples III, IV and morphine are shown in FIG. 14. Least squares analyses of these results indicated ED50 values of 0.64, 0.18 and 4.91 μmole/kg for the compounds of Examples III, IV and morphine, respectively. These results indicate that the compounds of Examples III and IV are 4.8- and 17.5-fold, respectively, more potent than morphine as analgesic agents.

A further investigation was conducted to determine the extent to which compounds of Examples III or IV might produce a more long lasting analgesic effect than morphine at doses higher than those used in the experiment described above. The analgesic effects of doses of morphine and the compound of Example III ranging from approximately 7- to 40-fold higher than their ED50 doses, and doses of the compound of Example IV ranging from approximately 12- to 75-fold higher than its ED50, were determined. Rats were injected S.C. with one of four doses of the compound of Example III, IV or morphine immediately following the determination of their baseline flick latencies and flick latencies were determined at 1, 2, 3, 4.5 and 6 h after drug administration. The doses used were 4.42, 8.85, 17.7 and 26.6 μmole/kg of the compound of Example III; 2.24, 4.48, 8.95 and 13.4 μmole/kg of the compound of Example IV; and 35.0, 70.1, 140 and 210 μmole/kg of morphine. The results for the compounds of Examples III, IV and morphine are shown in FIGS. 15, 16, and 17, respectively in which the data is expressed as a percentage of the maximum possible effect (% MPE). A 15 sec. cutoff latency was used to prevent tissue damage. The values shown are the means of 3-6 rats. As shown in these figures, neither compound, at doses at least as high as 40-times the ED50, produced longer-lasting analgesic effects than a comparable, in terms of multiples of the ED50, dose of morphine. None of the morphine-treated rats died during the course of the experiment. Out of six rats injected at each dose, the following number of deaths occurred during the experiment after the administration of the indicated compound: for the compound of Example III, 1 died at 8.85, and 3 died at 17.7 and 26.6 μmole/kg; for the compound of Example IV, 1 died at 4.48 and 8.95, and 2 died at 13.4 μmole/kg.

EXAMPLE XV

The antagonistic properties of the compounds of Examples XI and XII, i.e. inhibition of morphine-induced analgesia were assessed. Rats were injected IP with the antagonist followed immediately by the subcutaneous (S.C.) administration of 14 μmol/kg. morphine in a volume of 1 ml/kg saline and tail flick latencies were determined immediately prior to (baseline) as well as 40 minutes after drug administration.

Figure 18:
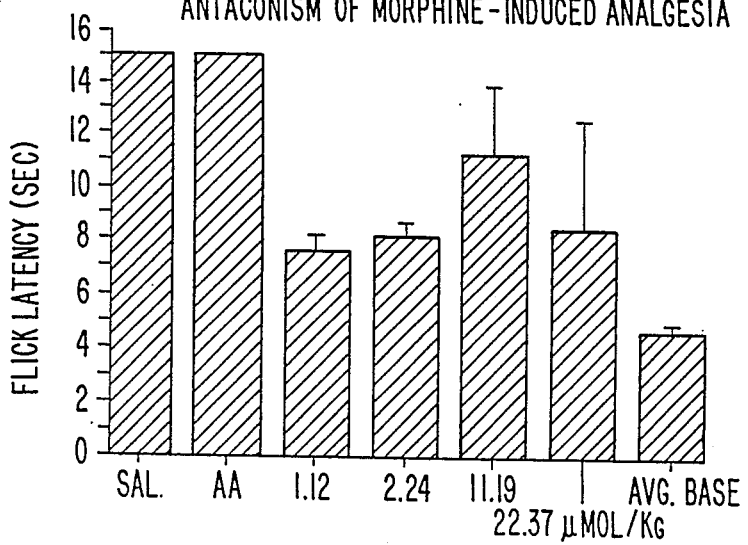
FIG. 18 is a graph illustrating the analgesic effect of 6-Benzyloximino-17-cyclopropylmethyl-4,5α-epoxy-3, 14-dihydroxymorphinan (compound XI of Example XI) on morphine - induced analgesia in rats.
Figure 19:
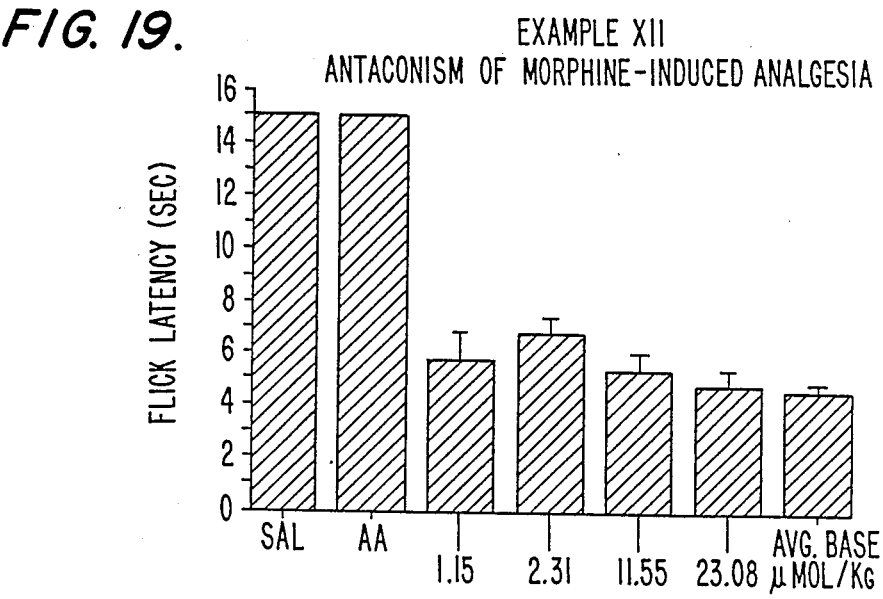
FIG. 19 is a graph illustrating the antagonism effect of 6-Phenyloximino-17-cyclopropylmethyl-4,5α-epoxy-3, 14-dihydroxymorphinan (compound XII of Example XII) of morphine - induced analgesia in rats.

Compounds of Examples XI and XII were injected intraperitoneally (I.P.) in a volume of 4 ml/kg of 0.3% acetic acid. The doses of the compound of Example XI were 1.12, 2.24, 11.19 and 22.37 μmol/kg, and 1.15, 2.31, 11.55 and 23.09 μmol/kg for the compound of Example XII. Tail flick latencies for the two antagonists are shown in FIGS. 18 and 19, and both compounds were able to antagonize the analgesia produced by morphine. In FIGS. 18 and 19 the doses for each group are expressed in μmol/kg. The data represents the mean ±SEM of 3 rats per group. The variability of the response after the two highest doses of the compound of Example XI is due to the small number of animals per group.

The ability of the compound of Example XII to antagonize morphine-induced analgesia after oral administration was evaluated and compared to that of naltrexone. Testing and drug administration were performed as described above. Naltrexone was administered in doses of 0.29, 1.47, 2.93, 14.66 and 29.33 μmol/kg, and dissolved in 0.9% saline in a volume of 1 ml/kg. The compound of Example XII was given in doses of 0.23, 1.15, 2.31, 11.55 and 23.09 μmol/kg, and dissolved in 0.3% acetic acid in a volume of 4 ml/kg. As illustrated in FIG. 21 the compound of Example XII was able to antagonize the analgesia produced by morphine, although it was less potent than naltrexone (FIG. 20). The data presented in FIGS. 20 and 21 represents the mean ±SEM of 4 rats per group.

EXAMPLE XVI

The appetite suppressing properties of the compound of Example XII were tested and compared to those of naltrexone. Rats were given water and powdered food ad lib for 8 days until food intake had stabilized, and body weight and food and water intakes were recorded at the same time every day. Animals were assigned to treatment groups matched on the basis of their 24 hr food consumption on the last baseline day, and rats were food deprived for 24 hr immediately before injection of the test compound. Naltrexone was administered S.C. at doses of 1.47, 2.93, 14.66 and 29.33 μmol/kg, in a volume of 1 ml/kg of 0.9% saline. The compound of Example XII was injected S.C. at doses of 1.15, 2.31, 11.55 and 23.09 μmol/kg, in a volume of 4 ml/kg of 0.3% acetic acid. Controls were injected with the vehicle solutions in the appropriate volumes. Food and water intakes were measured at 1, 3 and 24 hr after treatment. Data for each measure and time point were analyzed by one-way analysis of variance (ANOVA), and post-hoc comparisons were performed using Dunnett's test in order to compare the control mean to each of the treatment means.

Figure 22:
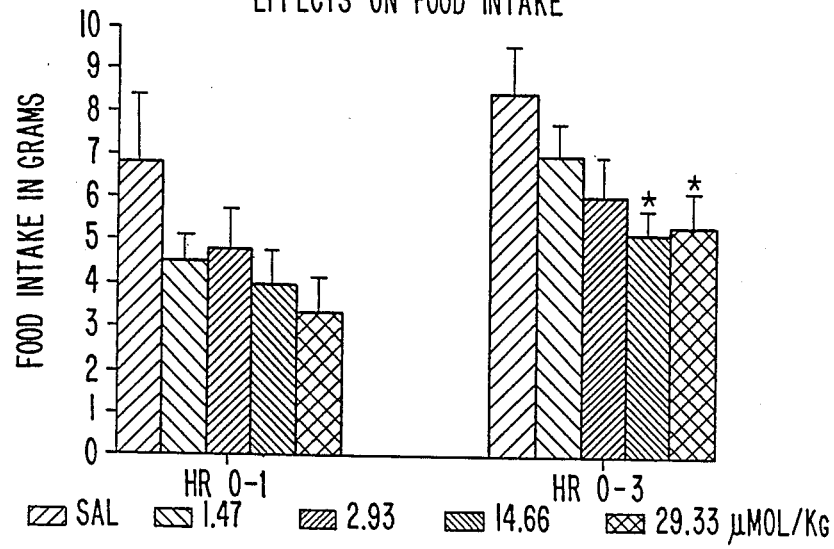
FIG. 22 is a graph illustrating the effect of naltrexone on the food intake in 24 hour food deprived rats.
Figure 23:
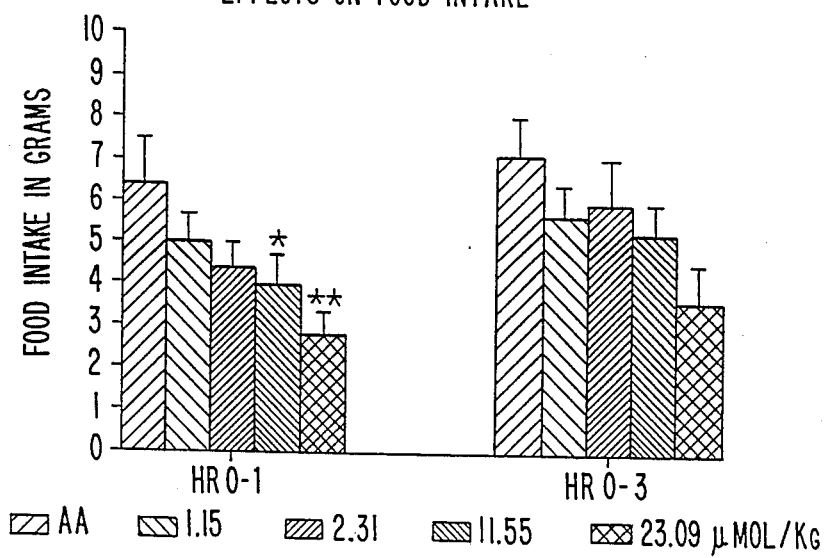
FIG. 23 is a graph illustrating the effect of 6-Phenyloximino-17-cyclopropylmethyl-4,5α-epoxy-3, 14-dihydroxymorphinan (compound XII of Example XII) on the food intake in 24 hour food deprived rats.

The data for food intake at 1 and 3 hr are presented in FIGS. 22 and 23. For the number of animals per group, see Table 3. The data in FIGS. 22 and 23 represent the mean ±SEM for each group. The * represents p>0.05 and **=p<0.001 (Dunnett's test) in FIGS. 22 and 23. ANOVA indicated a significant effect for naltrexone at 0-3 hr and the compound of Example XII at 0-1 hr. The compound of Example XII at 11.55 and 23.09 μmol/kg significantly inhibited feeding at 1 hr following administration, and the 14.66 and 29.33 μmol/kg doses of naltrexone inhibited feeding at 3 hr following treatment. Feeding had returned to control levels by 24 hr as shown in Table 3 below.

The effects of naltrexone and the compound of Example XII on water intake at 1 and 3 hr are illustrated in FIGS. 24 and 25. The ANOVAs for naltrexone at both 0-1 hr and 0-3 hr were significant. Naltrexone inhibited drinking at all doses tested at the 1 and 3 hr time points. No significant effects were observed for the compound of Example XII at any time point, and for both compounds water intake was equivalent to control levels by 24 hr as indicated in the following Table 3.

TABLE 3

EFFECTS OF NALTREXONE AND EXAMPLE XII ON 24 HR FOOD AND WATER CONSUMPTION IN 24 HR FOOD-DEPRIVED RATS

| Drug/Dose | N | Food Intake in Grams | Water Intake in mL |
|---|---|---|---|
| Saline | 5 | 40.0 ± 5.2 | 70.4 ± 11.3 |
| 0.3% Acetic Acid | 5 | 36.0 ± 3.5 | 72.4 ± 2.8 |
| Naltrexone | | | |
| 1.47 μmol/kg | 4 | 33.0 ± 0.7 | 69.0 ± 3.5 |
| 2.93 μmol/kg | 5 | 33.2 ± 3.0 | 62.4 ± 3.8 |
| 14.66 μmol/kg | 5 | 37.6 ± 4.2 | 53.4 ± 5.5 |
| 29.33 μmol/kg | 3 | 40.7 ± 8.2 | 66.0 ± 2.8 |
| Example XII | | | |
| 1.15 μmol/kg | 6 | 33.3 ± 1.6 | 68.3 ± 8.8 |
| 2.31 μmol/kg | 6 | 31.0 ± 2.0 | 65.0 ± 6.2 |
| 11.55 μmol/kg | 6 | 41.7 ± 7.4 | 60.3 ± 2.1 |
| 23.09 μmol/kg | 5 | 37.6 ± 5.6 | 62.8 ± 3.6 |

Rats were given water and powdered food for 8 days, and following this, animals were food deprived for 24 hr. Immediately prior to the feeding session on the following day, rats were injected S.C. with each compound at the doses indicated below. Data represent the mean ±SEM for each group.

It is evident that the compound of Example XII possesses anorectic activity for 1 hr after administration. Further, the compound of Example XII appears to have negligible effects on water intake, in contrast to naltrexone, which effectively inhibited drinking at all doses tested during the first three hours after administration. This effect may be due to a direct effect of naltrexone on drinking in addition to its effects on food intake, as has been reported previously (see G. A. Olson, R. D. Olson and A. J. Kastin. "Endogenous Opiates 1983": Peptides 5: 975-992, 1984). The decrease in feeding observed after treatment with naltrexone may be partly attributable to the decreased drinking that also occurs, whereas treatment with the compound of Example XII only affects feeding behavior.

A further experiment evaluated the time course of the anorectic effects of the compound of Example XII in comparison to naltrexone at higher doses. Testing was performed as described above, and baseline measurements were recorded for 7 days. Naltrexone was administered at doses of 14.66, 29.33, 58.65 and 117.30 μmol/kg, in a volume of 1 ml/kg of 0.9% saline. The compound of Example XII was injected at doses of 11.55, 23.09, 46.19 and 92.38 μmol/kg by suspension in a solution of 1:1 DMSO:water in a volume of 3 ml/kg. Food and water intakes were recorded at 1, 2, 4 and 6 h following treatment. The data for food intake are shown in Table 4 as illustrated below.

TABLE 4

TIME COURSE OF THE EFFECTS OF NALTREXONE AND THE COMPOUND OF EXAMPLE XII ON FOOD CONSUMPTION IN 24 HR FOOD-DEPRIVED RATS.

| | Cumulative Food Intake in Grams | | | |
|---|---|---|---|---|
| Drug/Dose | 0-1 Hr | 0-2 Hr | 0-4 Hr | 0-6 Hr |
| Saline | 6.4 ± 0.8 | 6.8 ± 0.9 | 8.8 ± 1.1 | 9.2 ± 1.1 |
| DMSO:H$_2$O | 5.2 ± 0.9 | 6.8 ± 1.3 | 7.6 ± 0.8 | 8.4 ± 0.5 |
| Naltrexone | | | | |
| 14.66 μmol/kg | 3.6 ± 0.5* | 3.6 ± 0.5* | 4.0 ± 0.0** | 5.2 ± 0.6** |
| 29.33 μmol/kg | 3.2 ± 0.6* | 3.2 ± 0.6** | 4.4 ± 0.5** | 5.2 ± 0.9** |
| 58.65 μmol/kg | 2.8 ± 1.1** | 2.8 ± 1.1** | 3.2 ± 0.9** | 6.4 ± 0.5 |
| 117.30 μmol/kg | 3.6 ± 0.8* | 3.6 ± 0.8* | 4.8 ± 0.9** | 7.6 ± 1.3 |
| Example XII | | | | |
| 11.55 μmol/kg | 2.0 ± 1.0** | 2.0 ± 1.0** | 2.8 ± 0.9** | 3.6 ± 1.3** |
| 23.09 μmol/kg | 2.0 ± 0.7** | 2.4 ± 0.8** | 3.6 ± 1.5** | 3.6 ± 1.5** |
| 46.19 μmol/kg | 2.8 ± 0.6 | 2.8 ± 0.6** | 3.2 ± 0.6** | 3.6 ± 0.8** |
| 92.38 μmol/kg | 3.2 ± 0.6 | 3.2 ± 0.6* | 4.0 ± 0.7* | 4.8 ± 1.1* |

See Table 3 for experimental details, except that baseline measures were record for 7 days. Immediately prior to the feeding session on the 8th day, rats were injected S.C. with naltrexone or the compound of Example XII at the doses indicated below. N=5 per group. Data represent the means ±SEM for each group. *=p<0.05; **=p<0.01 (Dunnett's test). ANOVA indicated significant effects for both naltrexone and the compound of Example XII at all time points. Naltrexone at all doses decreased feeding up to 4 hr after administration, and the two lower doses also decreased feeding at 6 hr post-treatment. All doses of the compounds of Example XII significantly decreased feeding from 2 to 6 hr following administration and the two lower doses decreased feeding up to 1 hr following admiistrastion.

The data for water intake are illustrated in Table 5 as reported below.

TABLE 5

TIME COURSE OF THE EFFECTS OF NALTREXONE AND THE COMPOUND OF EXAMPLE XII ON WATER CONSUMPTION IN 24 HR FOOD DEPRIVED RATS

| | Cumulative Water Intake in mL | | | |
|---|---|---|---|---|
| Drug/Dose | 0-1 Hr | 0-2 Hr | 0-4 Hr | 0-6 Hr |
| Saline | 9.0 ± 2.4 | 13.5 ± 2.6 | 23.3 ± 2.9 | 25.0 ± 4.3 |
| DMSO:H$_2$O | 7.0 ± 0.7 | 13.0 ± 1.5 | 18.5 ± 3.8 | 24.3 ± 3.6 |

TABLE 5-continued

TIME COURSE OF THE EFFECTS OF NALTREXONE AND THE COMPOUND OF EXAMPLE XII ON WATER CONSUMPTION IN 24 HR FOOD DEPRIVED RATS

| | Cumulative Water Intake in mL | | | |
|---|---|---|---|---|
| Drug/Dose | 0-1 Hr | 0-2 Hr | 0-4 Hr | 0-6 Hr |
| Naltrexone | | | | |
| 14.66 μmol/kg | 5.2 ± 1.1 | 9.2 ± 1.1* | 15.2 ± 2.0** | 22.8 ± 2.1 |
| 29.33 μmol/kg | 5.2 ± 0.6 | 8.4 ± 0.5* | 15.2 ± 1.1** | 21.6 ± 3.1 |
| 58.65 μmol/kg | 3.6 ± 0.8** | 6.8 ± 0.6** | 13.2 ± 1.3** | 22.4 ± 2.6 |
| 117.30 μmol/kg | 3.6 ± 0.8** | 9.2 ± 0.9* | 16.0 ± 1.6* | 26.8 ± 3.4 |
| Example XII | | | | |
| 11.55 μmol/kg | 4.8 ± 1.1 | 8.0 ± 1.2* | 15.6 ± 2.5 | 22.0 ± 1.6 |
| 23.09 μmol/kg | 4.0 ± 1.0 | 7.2 ± 0.6** | 13.2 ± 2.3 | 19.6 ± 2.2 |
| 46.19 μmol/kg | 5.2 ± 0.9 | 8.0 ± 1.6* | 15.2 ± 1.5 | 20.8 ± 2.9 |
| 92.38 μmol/kg | 4.0 ± 0.7 | 7.6 ± 0.8** | 15.2 ± 1.8 | 21.2 ± 2.1 |

See Table 3 for experimental details, except that baseline measurements were recorded for 7 days. Immediately prior to the feeding session on the 8th day, rats were injected S.C. with naltrexone or the compound of Example XII at the doses indicated. N=5 per group except Saline and DMSO where N=4. Data represent the mean ±SEM for each group. *=p<0.05; **=p<0.01 (Dunnett's test).

ANOVA for naltrexone revealed significant effects at 0-1 hr, 0-2 hr and 0-4 hr. The only effect noted for the compound of Example XII occurred at 0-2 hr. As in the previous experiment, the long-lasting effects of naltrexone on water intake were observed, while the effects of the compound of Example XII on drinking were much less apparent.

The plotting of data as a function of food intake/2 hr interval instead of cumulative food intake, shows that at the 4-6 hr interval, rats treated with the two highest doses of naltrexone are beginning to resume feeding, while feeding is still suppressed in animals treated with all doses examined of the compound of Example XII (FIGS. 26 and 27). As described above, significant decreases in feeding occur from 0-2 hr following administration of both compounds. Further, ANOVA indicated a significant effect for naltrexone at the 4-6 hr time interval that was due to an increase in food consumption at some doses compared to controls. The food intake of rats treated with the compound of Example XII did not "rebound" at any indicated dose in such a fashion, suggesting that the compound of Example XII at certain doses may have a longer duration of action than naltrexone at similar doses in causing anorexia, demonstrating its superiority as an appetite suppressant.

The ability of a compound to inhibit feeding may not be related to its anorectic properties, but rather to the ability of that compound to produce a conditioned taste aversion. This possibility was tested in the following experiment. Animals were adapted to water deprivation by restricting their access to water to a single 30 min presentation occurring at the same time every day. Baseline water intakes were determined for 7 days until intakes had stabilized, and animals were assigned to treatment groups based on their intakes on the final baseline day. On the following day (day 8), all rats received a bottle of condensed milk (diluted 2:1 water:- milk) in place of the water, and intakes were recorded for 30 min. Fifteen minutes after the milk was removed, rats were administered an I.P. injection of vehicles, LiCl (299.6 μmol/kg) or the compound of Example XII (1.15, 2.31, 11.55 and 23.09 μmol/kg). The compound of Example XII was dissolved in 0.3% acetic acid in a volume of 4 ml/kg. LiCl was dissolved in saline, and serves as a positive control, since it is a compound that reliably produces a strong conditioned taste aversion. This procedure was repeated on day 9. On day 10, all rats were given a two-bottle choice of water or the milk:water solution, and intakes were recorded for 30 min. Data for each experiment were analyzed by one-way ANOVA, and post-hoc comparisons were performed using Dunnett's test.

Figure 28:
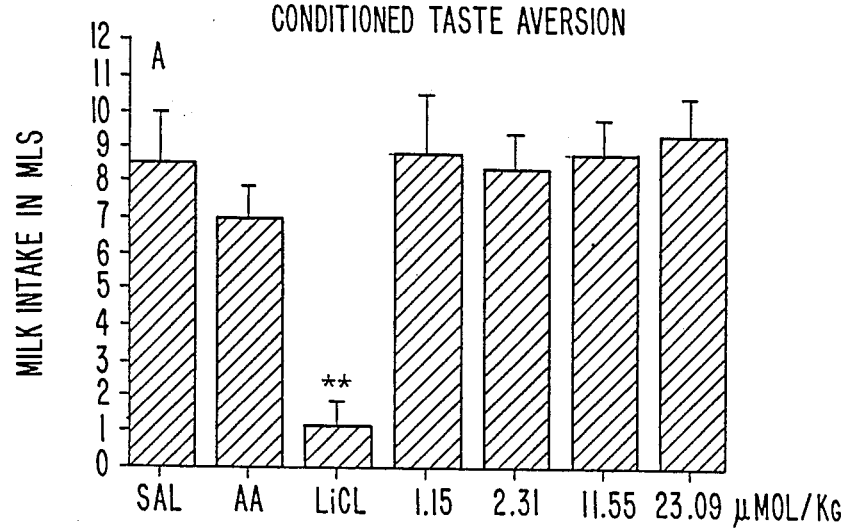
FIG. 28 is a graph illustrating the inability of various doses of 6-Phenyloximino-17-cyclopropylmethyl-4,5α-epoxy-3, 14-dihydroxymorphinan (compound XII of Example XII) to produce a conditioned taste aversion.
Figure 29:
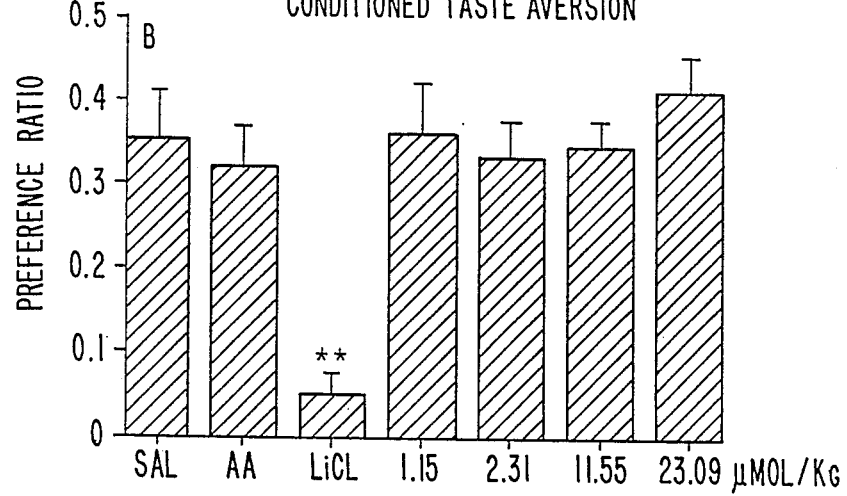
FIG. 29 is a graph illustrating the inability of various doses of 6- Phenyloximino-17-cyclopropylmethyl-4,5α-epoxy-3, 14-dihydroxymorphinan (compound XII of Example XII) to produce a conditioned taste aversion.

The effects of the compound of Example XII in producing a conditioned taste aversion are illustrated in FIGS. 28 and 29. In FIGS. 28 and 29 the data represent the mean ±SEM for each group. **=p<0.01 (Dunnett's test). Abbreviations: SAL, saline; AA, 0.3% acetic acid in distilled water; LiCl, lithium chloride. Doses of the compound of Example XII for each group are expressed in μmole/kg. The number of animals per group: SAL, 4; AA, LiCl and each dose of Example XII, 5. FIG. 28: Total milk intake in ml on day 10. FIG. 29: Preference ratio on day 10.

ANOVA indicated a significant effect, but significant decreases in milk intake and in the preference ratio were evident only for LiCl. The compound of Example XII was totally ineffective in producing a conditioned taste aversion at doses that exhibited anorectic properties.

The data confirm that anorectic doses of the compound of Example XII do not exert their effects on food intakes by decreasing water intake or by producing a conditioned taste aversion. This further indicates that this compound does not appear to cause any general malaise at doses up to 23.09 μmol/kg and only affects feeding behavior, further demonstrating its superiority as an appetite suppressant.

EXAMPLE XVII

The compound of Example XII was evaluated for its potency and duration in the antagonism of oxymorphonazine (OMZ)-induced analgesia. Naltrexone or the compound of Example XII was administered SC or PO immediately followed by SC treatment with 19 μmol/kg of OMZ, and tail flick latencies were determined at 0.5, 1, 1.5, 2, 3, 4, 6 and 8 hr after drug administration. Naltrexone was administered in a volume of 1 ml/kg of distilled H$_2$O, and the compound of Example XII was administered in a volume of 4 ml/kg for SC injections, and 8 ml/kg for PO injections, of 0.3% acetic acid. The doses for SC administration of naltrexone were 0.01, 0.03, 0.13, 0.27 and 1.33 μmol/kg, and 1.33, 2.65, 6.63, 13.26 and 26.53 μmol/kg for oral administration. The doses for SC administration of the compound of Example XII were 0.02, 0.21, 1.07, 2.13 and 10.66 μmol/kg, and 2.13, 5.33, 10.66, 21.32 and 42.64 μmol/kg for PO administration. Data represent the mean ±SEM of 4-5 animals per group.

As illustrated in FIG. 30, naltrexone, when given SC at a dose of 1.33 μmol/kg, maximally antagonized OMZ-induced analgesia for up to 1 hr, after which flick latencies began to return to control values. In contrast, SC administration of 10.66 μmol/kg of the compound of Example XII antagonized the analgesia produced by OMZ for the full eight hours of testing (FIG. 31). Lower doses by both routes of administration produced dose-dependent antagonism of the analgesia produced by OMZ. Following PO administration, naltrexone antagonized OMZ-induced analgesia for the longest time period at a dose of 26.53 μmol/kg, with a trend for progressive loss of the antagonistic effect over 0.5–4.0 hours, although the reversal was not complete by eight hours (FIG. 32). In contrast, when 42.64 μmol/kg of the compound of Example XII was administered PO, a 50% antagonism of analgesia was observed at 0.5 hours which remained very constant for a least eight hours (FIG. 33).

The above experiments confirm the prolonged duration of action of the compound of Example XII that was suggested by the feeding study data in Example XVI. Although the compound of Example XII was not as potent as naltrexone when administered by the oral route, its longer duration of action in the antagonism of OMZ-induced analgesia as described in Example XVII, and its ability to inhibit feeding without producing a conditioned taste aversion as described in Example XVI, indicate that the compound of Example XII is a novel and long-lasting opiate antagonist that exhibits superiority as an appetite suppressant.

While the invention has been described in terms of various preferred embodiments, the skilled artisan will appreciate that various modifications, substitutions, omissions and excipients may be made without departing from the spirit of the invention or the scope of the appended claims.

What is claimed is:

1. A potent, selective opioid receptor agonist or antagonist compound of the formula:

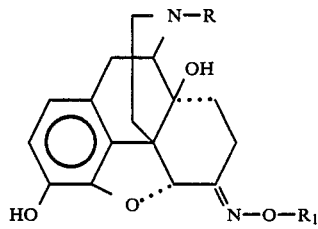

wherein R is methyl, allyl or cyclopropylmethyl and R$_1$ is 4-benzimidazolyl, 5-benzimidazolyl, benzyl or phenyl and the pharmaceutically acceptable salts thereof.

2. The potent, selective opioid receptor antagonist of claim 1 wherein R is allyl or cyclopropylmethyl and R$_1$ is 4-benzimidazolyl, 5-benzimidazolyl, benzyl or phenyl.

3. The compound according to claim 1 that is 6-Benzyloximino-17-methyl-4,5α-epoxy-3,14-dihydroxymorphinan.

4. The compound according to claim 1 that is 6-Phenyloximino-17-methyl-4,5α-epoxy-3,14-dihydroxymorphinan.

5. The compound according to claim 1 that is 6-Benzyloximino-17-allyl-4,5α-epoxy-3,14-dihydroxymorphinan.

6. The compound according to claim 1 that is 6-Phenyloximino-17-allyl-4,5α-epoxy-3,14-dihydroxymorphinan.

7. The compound according to claim 1 that is 6-Benzyloximino-17-cyclopropylmethyl-4,5α-epoxy-3,14-dihydroxymorphinan.

8. The compound according to claim 1 that is 6-Phenyloximino-17-cyclopropylmethyl-4,5α-epoxy-3,14-dihydroxymorphinan.

9. A pharmaceutical composition for relieving pain which comprises a pain relieving effective amount of one or more compounds of claim 1 wherein R is methyl with a pharmaceutically acceptable carrier and/or diluent.

10. A process of relieving pain in an animal in need thereof which comprises administering said compound of claim 9 parenterally, nasally, orally, rectally or a combination thereof to said animal in need thereof.

11. A pharmaceutical composition for treating opiate drug abuse which comprises administering an effective amount of one or more compounds of claim 1 wherein R is allyl or a cyclopropylmethyl with a pharmaceutically acceptable carrier and/or diluent.

12. A process for treating opiate drug abuse in an animal in need thereon which comprises administering said compound of claim 2 said composition of claim 11 parenterally, orally, nasally, rectally or a combination thereof to said animal in need thereof.

13. A pharmaceutical composition for suppressing appetite which comprises administering an effective amount of one or more compounds of claim 1 wherein R is allyl or cyclopropylmethyl with a pharmaceutically acceptable carrier and/or diluent.

14. A process for suppressing appetite in an animal in need thereof which comprises administering said compound of claim 2 or said composition of claim 13 parenterally, orally, nasally, rectally or a combination thereof to said animal in need thereof.

15. A potent, selective opioid receptor agonist compound of the formula;

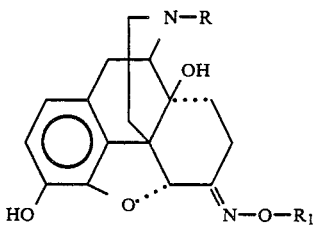

wherein R is methyl and $R_1$ is a naphthyl, tetrahydronaphthyl, phenylethyl, 4-benzimidazolyl, 5 benzimidazolyl,

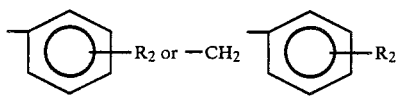

wherein $R_2$ is selected from the group comprising a hydrogen, halogen, hydroxy, nitro, methoxy, methyl, trifluoromethyl or amino and the pharmaceutically acceptable salts thereof.

16. The potent, selective opioid receptor agonist of claim 15 for relieving pain wherein said compound is 6-Benzyloximino-7-methyl-4,5α-epoxy-3, 14-dihydroxymorphinan or 6-PHenyloximino-17-methyl-4, 5α-epoxy-3, 14-dihydroxymorphinan and the pharmaceutically acceptable salts or mixtures thereof.

17. A process for relieving pain in an animal in need thereof which comprises administering said compound of claim 16 parenterally, nasally, orally, rectally or a combination thereof to said animal in need thereof.

18. The potent, selective opioid receptor agonist or antagonist of the formula:

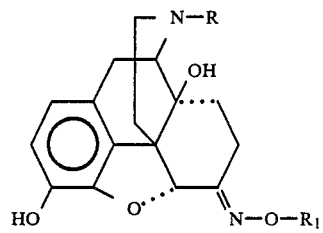

wherein R is methyl, allyl or cyclopropylmethyl and wherein $R_1$ is a naphthyl, tetrahydronaphthyl, phenylethyl, 4-benzimidazolyl, 5 benzimidazolyl,

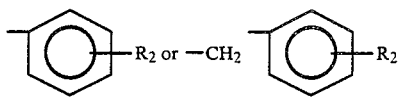

wherein $R_2$ is selected from the group comprising a hydrogen, halogen, hydroxy, nitro, methoxy, methyl, trifluoromethyl or amino and the pharmaceutically acceptable salts thereof.

19. The potent, selective opioid receptor antagonist of claim 18 for treatment of opiate drug abuse wherein said compound is 6-Benzyloximino-17-cyclopropylmethyl-4,5α-epoxy-3,14-dihydroxymorphinan or 6-Phenyloximino-17-cyclopropylmethyl-4,5α-epoxy-3,14-dihydroxymorphinan and the pharmaceutically acceptable salts or mixtures thereof.

20. A process for relieving opiate drug abuse in an animal in need thereof which comprises administering said compound of claim 19 parenterally, nasally, orally, rectally or a combination thereof to said animal in need thereof.

21. The potent, selective opioid receptor antagonist of claim 18 for suppressing appetite wherein said compound is 6-Phenyloximino-17-cyclopropylmethyl-4,5α-epoxy-3,14-dihydroxymorphinan and the pharmaceutically acceptable salts or mixtures thereof.

22. A process for suppressing appetite in an animal in need thereof which comprises administering said compound of claim 21 parenterally, nasally, orally, rectally or a combination thereof to said animal in need thereof.

* * * * *